(12) United States Patent
Fujisaki et al.

(10) Patent No.: US 10,987,122 B2
(45) Date of Patent: Apr. 27, 2021

(54) ULTRASONIC PROBE

(71) Applicant: OLYMPUS CORPORATION, Hachioji (JP)

(72) Inventors: Ken Fujisaki, Sagamihara (JP); Takamitsu Sakamoto, Hachioji (JP); Hiroyuki Araki, Hachioji (JP); Hideto Yoshimine, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 170 days.

(21) Appl. No.: 16/394,477

(22) Filed: Apr. 25, 2019

(65) Prior Publication Data

US 2019/0247081 A1 Aug. 15, 2019

Related U.S. Application Data

(63) Continuation of application No. PCT/JP2017/026492, filed on Jul. 21, 2017.

(30) Foreign Application Priority Data

Oct. 28, 2016 (JP) .............................. JP2016/082178

(51) Int. Cl.
*A61B 17/32* (2006.01)
*A61B 17/16* (2006.01)

(52) U.S. Cl.
CPC ...... *A61B 17/320068* (2013.01); *A61B 17/16* (2013.01); *A61B 17/1659* (2013.01);
(Continued)

(58) Field of Classification Search
CPC .................. A61B 17/16; A61B 17/32; A61B 2017/320008; A61B 17/320068;
(Continued)

(56) References Cited

U.S. PATENT DOCUMENTS 4,832,683 A * 5/1989 Idemoto ........... A61B 17/32006
604/22
5,250,061 A * 10/1993 Michelson ......... A61B 17/1671
606/160

(Continued)

FOREIGN PATENT DOCUMENTS

JP H10-295700 A 11/1998
JP 2010-335 A 1/2010
(Continued)

OTHER PUBLICATIONS

Apr. 30, 2019 International Preliminary Report on Patentability issued in International Application No. PCT/JP2016/082178.
(Continued)

*Primary Examiner* — Larry E Waggle, Jr.
(74) *Attorney, Agent, or Firm* — Oliff PLC

(57) ABSTRACT

An ultrasonic probe includes a treatment portion that has a through-hole or concave portions. The through-hole extends from a first outer surface to a second outer surface facing in an opposite direction to that of the first outer surface. The concave portions include a first concave portion on the first outer surface, and a second concave portion on the second outer surface. The treatment portion includes a blade formed along an edge of an opening of the through-hole or the first concave portion. An outer relay surface extends from the blade to the second outer surface and faces away from a center axis of the through-hole or the concave portions. A distance from the center axis to the blade is greater than or equal to a distance from the center axis to the outer relay surface at a position between the blade and the second outer surface.

15 Claims, 10 Drawing Sheets

(52) U.S. Cl.
CPC .......... *A61B 17/1675* (2013.01); *A61B 17/32* (2013.01); *A61B 2017/320008* (2013.01); *A61B 2017/320077* (2017.08); *A61B 2217/005* (2013.01)

(58) Field of Classification Search
CPC ....... A61B 2017/320072; A61B 2017/320074; A61B 2017/320077; A61B 2017/320078
See application file for complete search history.

(56) References Cited

U.S. PATENT DOCUMENTS

| | | | |
|---|---|---|---|
| 6,398,793 B1 | 6/2002 | McGuire | |
| 2005/0090829 A1* | 4/2005 | Martz | A61B 17/1604 606/79 |
| 2009/0018489 A1 | 1/2009 | Babaev | |
| 2009/0018491 A1 | 1/2009 | Babaev | |
| 2009/0216179 A1 | 8/2009 | Babaev et al. | |
| 2009/0318945 A1 | 12/2009 | Yoshimine et al. | |
| 2011/0160624 A1 | 6/2011 | Babaev | |
| 2015/0142033 A1 | 5/2015 | Stulen et al. | |
| 2016/0143648 A1* | 5/2016 | Onuma | A61B 17/32 606/79 |
| 2016/0157884 A1 | 6/2016 | Oniuma et al. | |
| 2017/0367727 A1 | 12/2017 | Sakai | |

FOREIGN PATENT DOCUMENTS

| | | |
|---|---|---|
| JP | 5784863 B1 | 9/2015 |
| JP | 5836540 B2 | 12/2015 |
| WO | 2017/013887 A1 | 1/2017 |

OTHER PUBLICATIONS

Apr. 30, 2019 International Preliminary Report on Patentability issued in Internation Application No. PCT/JP2017/026492.

Oct. 10, 2017 International Search Report issued in International Patent Application No. PCT/JP2017/026492.

Jan. 5, 2021 Office Action issued in Chinese Patent Application No. 201780066438.1.

* cited by examiner

ULTRASONIC PROBE

This is a Continuation Application of PCT Application No. PCT/JP2017/026492, filed Jul. 21, 2017 and based upon and claiming the benefit of priority from prior PCT Application No. PCT/JP2016/082178, filed Oct. 28, 2016, the entire contents of which are incorporated herein by reference.

BACKGROUND

Exemplary embodiments relate to an ultrasonic transducer including a piezoelectric element which is configured to generate ultrasonic vibration by an electric energy being supplied, and a method of manufacturing the ultrasonic transducer.

US 2016/0157884 A1 discloses an ultrasonic probe configured to abrade bone or cartilage as a treatment object by using transmitted ultrasonic vibration. In a distal portion of the probe, a treating portion is provided, and in an example, the treating portion has a so-called curette shape. Here, a direction along the center axis of the treating portion is defined as an extending direction of the treating portion. The curette-shaped treating portion includes a first outer surface facing a direction intersecting the extending direction of the treating portion, and a second outer surface facing a side opposite to the side to which the first outer surface is facing. The curette-shaped treating portion further has a through-hole extending from the first outer surface to the second outer surface. At a first opening created by the through-hole in the first outer surface, a first blade is formed along an edge of the first opening, and at a second opening created by the through-hole in the second outer surface, a second blade is formed along an edge of the second opening. The treatment object is abraded by causing the treating portion to vibrate per ultrasonic vibration while contacting the treatment object with the first blade or the second blade.

SUMMARY

According to an exemplary embodiment, an ultrasonic probe includes: a probe main body to which ultrasonic vibration generated by a transducer is transmitted; and a treatment portion provided on a distal side with respect to the probe main body. The treatment portion is configured to excise bone or cartilage as a treatment object by the ultrasonic vibration, and the treatment portion includes a first outer surface including a first concave portion, and a second outer surface facing in a direction opposite to the first outer surface, and including a second concave portion. The first concave portion and the second concave portion are coaxially disposed about a center axis that intersects an extending direction of the treatment portion such that the first concave portion and the second concave portion are concave in opposite directions along the center axis. The treatment portion further includes: a first blade formed along an edge of an opening of the first concave portion, a second blade formed along an edge of an opening of the second concave portion, and an outer relay surface which extends from the first blade to the second blade and faces away from the center axis of the first and second concave portions. A distance from the center axis of the first and second concave portions to the first blade is greater than or equal to a distance from the center axis to the outer relay surface at a position between the first blade and the second blade. The first concave portion includes a first inner relay surface extending from the opening of the first concave portion to a bottom surface of the first concave portion. The first inner relay surface includes a first inner sloped surface extending from the opening of the first concave portion toward the bottom surface of the first concave portion. The first inner sloped surface is sloped in a direction from the opening of the first concave portion towards the center axis. The second concave portion includes a second inner relay surface extending from the opening of the second concave portion to a bottom surface of the second concave portion. The second inner relay surface includes a second inner sloped surface extending from the second opening towards the bottom surface of the second concave portion. The second inner sloped surface is sloped in a direction from the opening of the second concave portion towards the center axis.

According to another exemplary embodiment, an ultrasonic probe includes: a probe main body to which ultrasonic vibration generated by a transducer is transmitted; and a treatment portion provided on a distal side with respect to the probe main body. The treatment portion is configured to excise bone or cartilage as a treatment object by the ultrasonic vibration, and the treatment portion includes a first outer surface, and a second outer surface facing in a direction opposite to the first outer surface. The treatment portion has a through-hole that extends from the first outer surface to the second outer surface along a center axis intersecting an extending direction of the treatment portion. An outer periphery of the through-hole is defined by an inner relay surface extending from a first outer surface opening of the through-hole to a second outer surface opening of the through-hole. The inner relay surface includes a first inner sloped surface extending from the first outer surface opening of the through-hole towards a second outer surface side, and a second inner sloped surface extending from the second outer surface opening of the through-hole towards a first outer surface side. The first inner sloped surface is sloped in a direction from the first outer surface opening of the through-hole towards the center axis, and the second inner sloped surface is sloped in a direction from the second outer surface opening of the through-hole towards the center axis. The treatment portion also includes a first blade formed along an edge of the first outer surface opening of the through-hole, and an outer relay surface which extends from the first blade to the second outer surface and faces a side away from a center axis of the through-hole. A distance from the center axis of the through-hole to the first blade is greater than or equal to a distance from the center axis to the outer relay surface at a position between the first blade and the second outer surface.

Advantages will be set forth in the description which follows, and in part will be apparent from the description, or may be learned by practice of exemplary embodiments. The advantages may be realized and obtained by means of the instrumentalities and combinations particularly pointed out hereinafter.

BRIEF DESCRIPTION OF THE DRAWING

The accompanying drawings, which are incorporated in and constitute a part of the specification, illustrate exemplary embodiments.

DETAILED DESCRIPTION

An exemplary embodiment will be described with reference to FIGS. 1 to 13.

Figure 1:
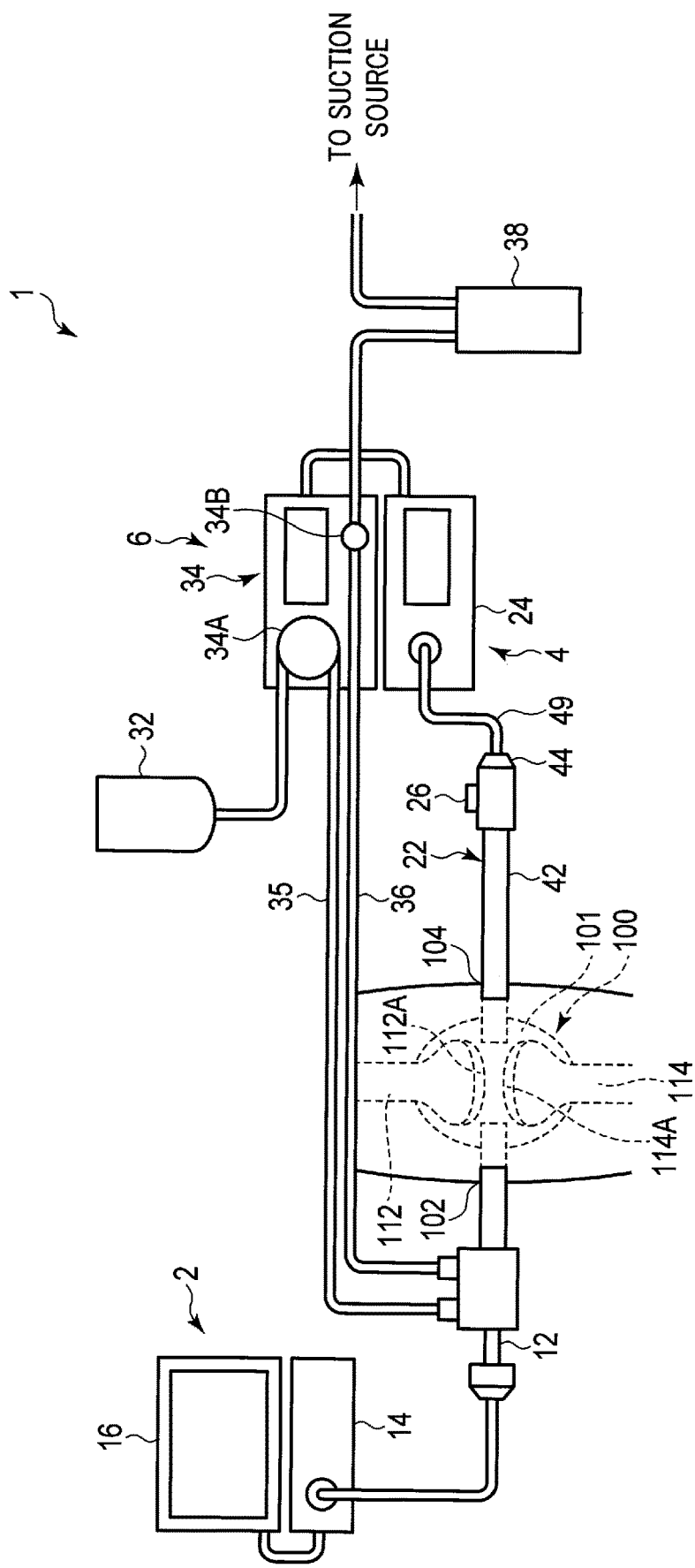
FIG. 1 is a schematic view showing a treatment system according to an exemplary embodiment.

FIG. 1 is a view showing a treatment system 1 according to an exemplary embodiment. As shown in FIG. 1, the treatment system 1 is used, for example, when treating a knee joint 100. The treatment system 1 includes an arthroscopic device 2, a treatment device 4, and a perfusion device 6.

The arthroscopic device 2 includes an arthroscope 12 configured to observe an inside of a patient's knee joint 100, that is, the inside of a patient's joint cavity 101, an arthroscopic controller 14, such as an image processor, configured to perform image processing based on a subject image captured by the arthroscope 12, and a monitor 16 configured to display an image generated by image processing using the arthroscopic controller 14. The arthroscope 12 is inserted into the joint cavity 101 of the knee joint 100 through a first portal 102, the patient's knee joint 100 being communicated with the outside of the skin via the first portal 102. The position of the first portal 102 is not set to a single location but rather set appropriately according to a patient's condition, position of the treatment object and the like. It is also preferable that a cannula (not shown) be provided in the first portal 102, and that the arthroscope 12 be inserted via the cannula into the joint cavity 101 of the knee joint 100.

The treatment device 4 includes a treatment unit 22, a controller 24, and an operating member 26. Although the operating member 26 of the embodiment shown FIG. 1 is an operating button integral with the treatment unit 22, the operating member 26 may, in an embodiment, be a foot switch or a keyboard separated from the treatment unit 22. The controller 24 controls a supply of electric energy (electric power) to the treatment unit 22 according to an input operation at the operating member 26. For example, the electric energy output from the controller 24 to the treatment unit 22 is kept while pushing the operating member 26, and when the operating member 26 is released, the electric energy from the controller 24 to the treatment unit 22 is stopped. In an embodiment, a plurality of operating members 26 may be provided, and, upon performing an input operation, a magnitude of the electric energy output from the controller 24 may be different for each operating member 26.

The treatment unit 22 is inserted into the joint cavity 101 of the knee joint 100 via a second portal 104, the patient's knee joint 100 being communicated with the outside of the skin via the second portal 104. The position of the second portal 104 is not set to a single location but rather set appropriately according to a patient's condition, position of the treatment object and the like. It is also preferable that a cannula (not shown) be provided in the second portal 104, and that the treatment unit 22 be inserted via the cannula into the joint cavity 101 of the knee joint 100. It should be noted that although the arthroscope 12 and the treatment unit 22 shown in FIG. 1 face each other in the joint cavity 101, the arthroscope 12 and the treatment unit 22 are arranged so that their positional relationship is appropriate according to the position of the treatment object and the like.

The perfusion device 6 includes a liquid source 32 configured to contain a perfusion liquid such as a saline, a perfusion pump unit 34, a liquid-supplying tube 35 one end of which is connected to the liquid source 32, a liquid-draining tube 36, and a suction bottle 38 to which one end of the liquid-draining tube 36 is connected. The suction bottle 38 is connected to a suction source attached to a wall of a surgery room. By actuating a liquid-supplying pump 34A of the perfusion pump unit 34, the perfusion liquid is supplied from the liquid source 32 via the liquid-supplying tube 35. The perfusion pump unit 34 is further provided with a pinch valve 34B as a drain valve. By switching between opening and closing the pinch valve 34B, it is possible to switch between a state in which the perfusion liquid inside the joint cavity 101 of the knee joint 100 is sucked through the liquid-draining tube 36 into the suction bottle 38 and a state in which the suction of the perfusion liquid inside the joint cavity 101 is stopped.

The other end of the liquid-supplying tube 35, which is a liquid-supplying conduit, is connected to the arthroscope 12. The perfusion liquid can thus be supplied via the arthroscope 12 into the joint cavity 101 of the knee joint 100. The other end of the liquid-draining tube 36, which is a liquid-draining conduit, is connected to the arthroscope 12. The perfusion liquid can therefore be discharged via the arthroscope 12 from inside the joint cavity 101 of the knee joint 100. It should be noted that the other end of the liquid-supplying tube 35 may be connected to the treatment unit 22 and may be capable of supplying the perfusion liquid via the treatment unit 22 into the joint cavity 101 of the knee joint 100. Further, the other end of the liquid-draining tube 36 may be connected to the treatment unit 22, and may discharge the perfusion liquid via the treatment unit 22 from inside the joint cavity 101. Moreover, the perfusion fluid may be supplied into or discharged from the joint space 101 via a portal other than the first portal 102 into which the arthroscope 12 is inserted and the second portal 104 into which the treatment unit 22 is inserted.

Figure 2:
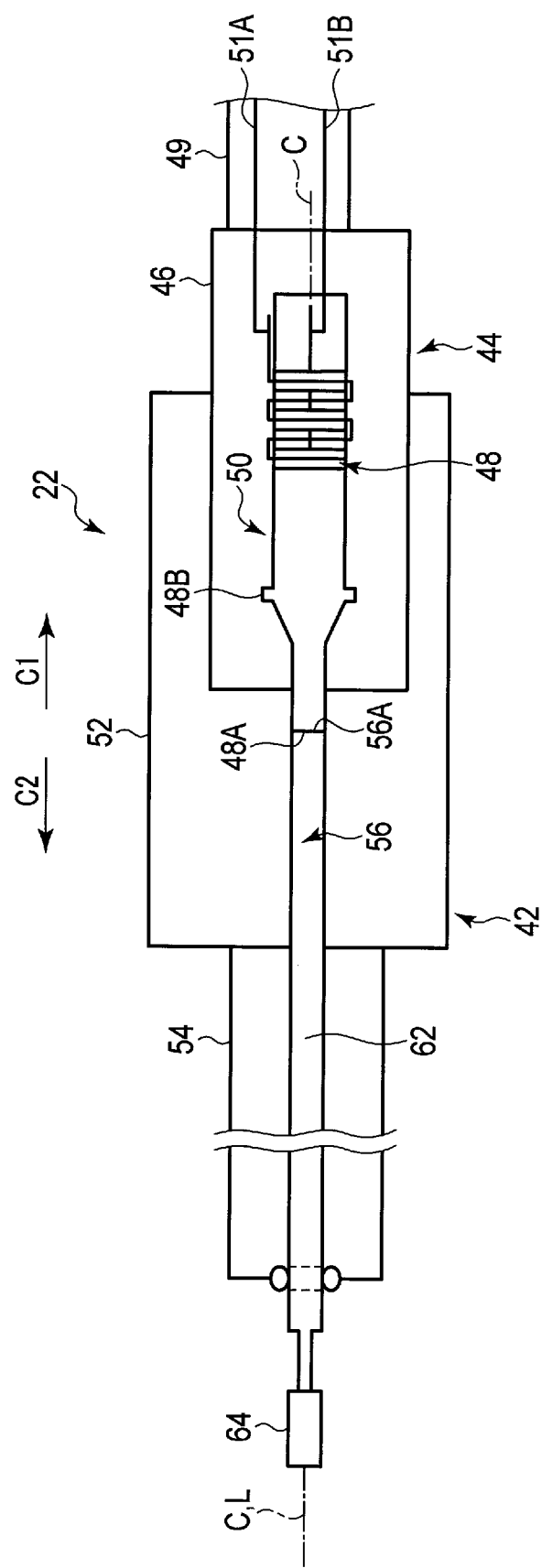
FIG. 2 is a schematic view showing a configuration of a treatment unit of an exemplary embodiment.

FIG. 2 is a view showing a configuration of the treatment unit 22. As shown in FIG. 2, the treatment unit includes an ultrasonic treatment instrument 42, and a transducer unit 44. Although it is preferable that the transducer unit 44 be detachably attached to the ultrasonic treatment instrument 42, the ultrasonic treatment instrument 42 may be integral with the transducer unit 44. The transducer unit 44 includes a housing (transducer case) 46, and a bolt-clamped Langevin-type transducer 48. At a distal end of the transducer 48, a connecting portion 48A is formed. It is preferable that the connecting portion 48A protrude to a distal side of a housing 46 in a direction along a center axis C of the transducer 48. The housing 46 supports a supported portion 48B of the transducer 48.

One end of a cable 49 is connected to the housing 46 of the transducer unit 44, while the other end of the cable 49 is connected to the controller 24. Electrical wirings 51A, 51B extend through the cable 49. One end of the electric wirings 51A, 51B is connected to the transducer 48, while the other end of the electric wirings 51A, 51B is connected to the controller 24. The electric energy output from the controller 24 is supplied to the transducer 48 via the electrical wirings 51A, 51B. AC power as electric energy is supplied to the transducer 48 at any frequency within a predetermined frequency range. The electric energy supplied to the transducer 48 causes the transducer 48 to generate an ultrasonic vibration.

The ultrasonic treatment instrument 42 includes a housing (handle) 52, a tubular body (outer tube) 54 extending from the housing 52 along the center axis C, and an ultrasonic probe 56 inserted through the tubular body 54. Here, in the ultrasonic treatment instrument 42, the side on which the housing 52 is positioned with respect to the tubular body 54 is defined as the proximal side (arrow C1 side), while the side opposite to the proximal side is defined as the distal side (arrow C2 side). The tubular body 54 is attached to the housing 52 from the distal side. Further, in the embodiment, the tubular body 54 is substantially coaxial with the transducer 48. The housing 52 and the tubular body 54 of the ultrasonic treatment instrument 42 are formed of an electrically insulating material. The housing 46 of the transducer unit 44 is detachably coupled to the housing 52 of the ultrasonic treatment instrument 42. It should be noted that it is preferable that the housing 52 of the ultrasonic treatment instrument 42 and the housing 46 of the transducer unit 44 be integral with each other.

It should further be noted that a rotating knob (not shown) may be attached as a rotation operating member to the housing 52 of the ultrasonic treatment instrument 42. The rotating knob is rotatable with respect to the housing 52 around the center axis C of the tubular body 54. By rotating the rotating knob, the housing 46, the transducer 48, the tubular body 54, and the ultrasonic probe 56 of the transducer unit 44 rotate together with respect to the housing 52 around the center axis C of the tubular body 54.

The ultrasonic probe 56 is made of a highly vibration-transmitting material such as, for example, a titanium alloy material. At a proximal end of the ultrasonic probe 56, a connecting portion 56A is formed. By connecting the transducer unit 44 to the housing 52, the connecting portion 56A of the ultrasonic probe 56 is connected to the connecting portion 48A of the transducer 48. By connecting the ultrasonic probe 56 to a distal side of the transducer 48, the ultrasonic vibration generated by the transducer 48 is transmitted to the ultrasonic probe 56. In the ultrasonic probe 56, the ultrasonic vibration is transmitted from the proximal side to the distal side.

While the ultrasonic vibration generated by the transducer 48 is transmitted in the ultrasonic probe 56, the transducer 48 and the ultrasonic probe 56 become a vibrating body 50 caused by the ultrasonic vibration to vibrate together. As mentioned, AC power is supplied to the transducer 48 at any frequency within the predetermined frequency range. Therefore, while the ultrasonic vibration is transmitted via the ultrasonic probe 56, the vibrating body 50 vibrates at any resonance frequency within a predetermined frequency range. In this case, a direction of vibration of the vibrating body 50 is substantially parallel to a longitudinal direction of the vibrating body 50, that is, along the center axis C of the tubular body 54. While the vibrating body 50 vibrates at any resonance frequency within the predetermined frequency range, anti-nodes are generated at the distal end and the proximal end of the vibrating body 50.

It should be noted that in the embodiment provided with the plurality of operating members 26 and in which the magnitude of the electric energy output from the controller 24 is different for each operating member 26, the magnitude of the electric energy supplied to the transducer 48 is different for each operating member 26. For this reason, the vibration energy of the generated ultrasonic vibration is different for each operating member 26, and the magnitude of the amplitude at the ultrasonic probe 56 when an input operation is performed is different.

As shown in FIG. 2, the ultrasonic probe 56 includes a probe main body 62, and a treating portion (distal portion) 64 provided on a distal side with respect to the probe main body 62 and capable of excising bone and cartilage as an treatment object by ultrasonic vibration. The probe main body 62 is substantially coaxial with the tubular body 54 and has the same center axis C as the tubular body 54. The treating portion 64 protrudes from a distal end of the tubular body 54 to the distal side. The ultrasonic vibration generated by the transducer 48 is transmitted to the probe main body 62, and subsequently through the probe main body 62 to the treating portion 64.

In an embodiment, the treating portion 64 is provided coaxially with the probe main body 62 and extends straight from the probe main body 62 toward the distal side. In this case, a center axis L of the treating portion 64 coincides with the center axis C of the probe main body 62. In another embodiment, the treating portion 64 is bent or curved with respect to the probe body portion 62. In this case, the center axis L of the treating portion 64 is bent or curved with respect to the center axis C of the probe main body 62.

Figure 3:
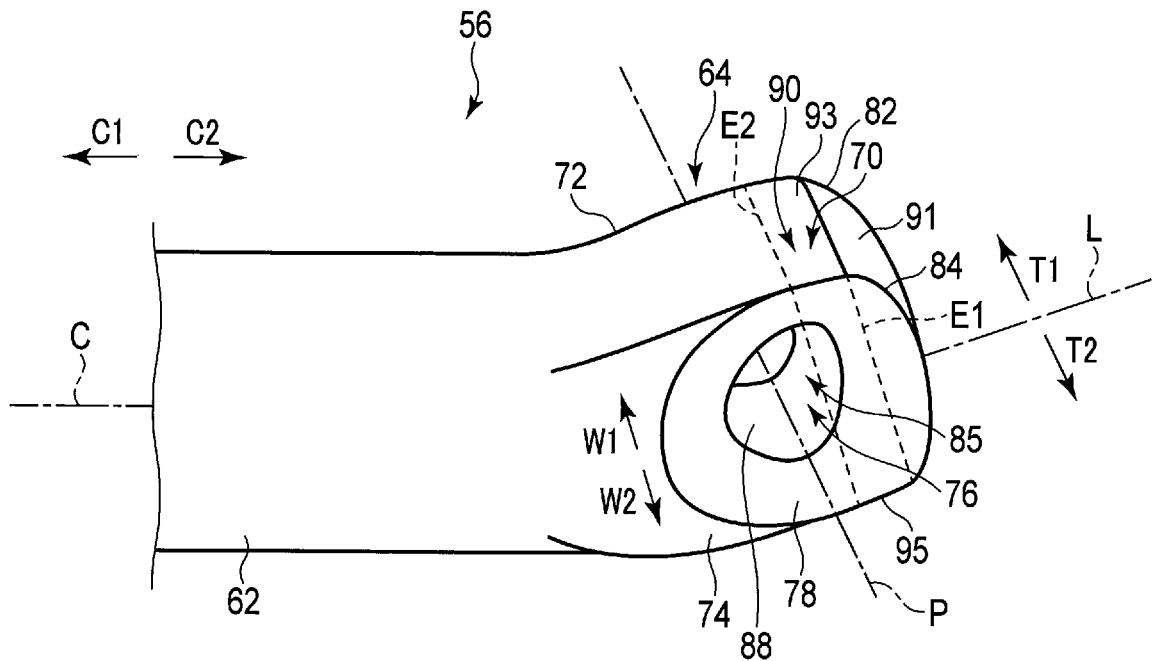
FIG. 3 is a perspective view schematically showing a configuration of a treating portion of the ultrasonic treatment instrument of an exemplary embodiment.
Figure 4:
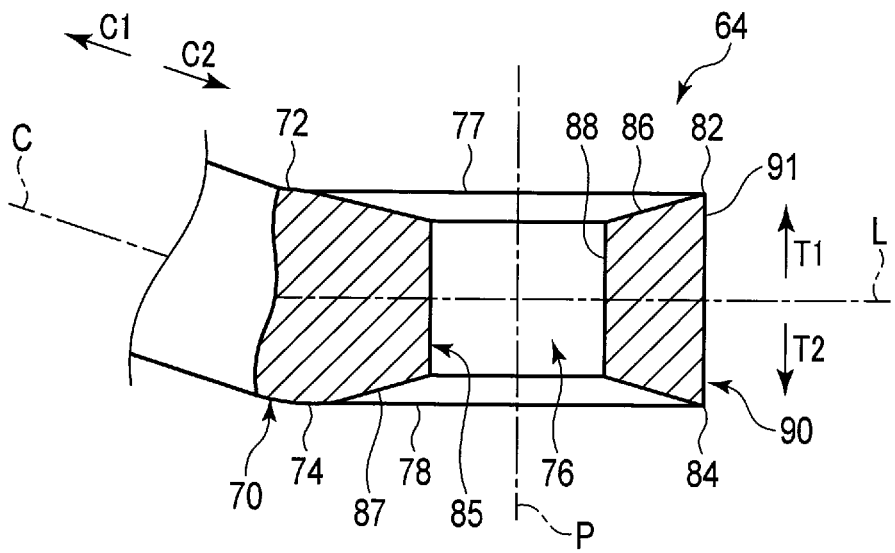
FIG. 4 is a cross-sectional view of the ultrasonic treatment instrument of an exemplary embodiment, schematically showing the configuration of the treating portion.

FIGS. 3 and 4 are views showing a configuration of the treating portion 64. As shown in FIGS. 3 and 4, the treating portion 64 extends along the center axis L. Also, the treating portion 64 has an outer surface 70 exposed outward. Here, the direction along the center axis L of the treating portion 64 is the extending direction of the treating portion 64. The outer surface 70 includes a first outer surface 72 facing a predetermined direction intersecting (substantially perpendicular to) the extending direction of the treating portion 64, and a second outer surface 74 facing an opposite side of the side where the first outer surface 72 faces. Moreover, a through-hole 76 penetrating the treating portion 64 is formed in the treating portion 64 from the first outer surface 72 to the second outer surface 74. The through-hole 76 extends along the center axis P. The extending direction of the through-hole 76, that is, the direction along the center axis P intersects (is substantially perpendicular to) the extending direction of the treating portion 64. Here, the extending direction of the through-hole 76 is substantially parallel to a thickness direction (direction indicated by the arrows T1 and T2) of the treating portion 64. Further, the direction intersecting (being substantially perpendicular to) the center axis L of the treating portion 64 and intersecting (being substantially perpendicular to) the center axis P of the through-hole 76 is the width direction of the treating portion 64 (direction indicated by the arrows W1 and W2). Therefore, in the embodiment, the first outer surface 72 faces one side (arrow T1 side) in the thickness direction of the treating portion 64, while the second outer surface 74 faces the other side (arrow T2 side) in the thickness direction of the treating portion 64. FIG. 4 shows the treating portion 64 in a cross section substantially perpendicular to the width direction.

The through-hole 76 opens both at a first opening 77 in the first outer surface 72 and at a second opening 78 in the second outer surface 74. In the first outer surface 72, a first blade 82 along an edge of the first opening 77 is formed, and in the second outer surface 74, a second blade 84 along an edge of the second opening 78 is formed. Each of the first blade 82 and the second blade 84 extends around a center axis P of the through-hole 76. The first blade 82 is provided in a region on the distal side at the edge of the first opening 77, and the second blade 84 is provided in a region on the distal side at the edge of the second opening 78. Since this embodiment has the mentioned configuration, the treating portion 64 of the embodiment is curette-shaped. Moreover, in the embodiment, the cross-sectional shape substantially perpendicular to the center axis P of the through-hole 76 is substantially pentagonal, and the shape of the region surrounded by each of the edge of the first opening 77 and the edge of the second opening 78 is substantially pentagonal.

The treating portion 64 includes an inner relay surface 85 forming an outer periphery (outer edge) of the through-hole 76. The inner relay surface 85 extends from the first opening 77 of the first outer surface 72 to the second opening 78 of the second outer surface 74 along the thickness direction of the treating portion 64. The through-hole 76 is surrounded by the inner relay surface 85. The inner relay surface 85 faces a side approximating the center axis P of the through-hole 76 in radial direction of the through-hole 76. The inner relay surface 85 includes a first inner sloped surface (first blade-forming surface) 86 extending from the first opening 77 towards the second outer surface 74, a second inner sloped surface (second blade-forming surface) 87 extending from the second opening 78 towards the first outer surface 72, and an inner extending surface 88 continuing between the first inner sloped surface 86 and the second inner sloped surface 87 in the extending direction of the through-hole 76.

Each of the first inner sloped surface 86 and the second inner sloped surface 87 is sloped with respect to the thickness direction of the treating portion 64, that is, the extending direction of the through-hole 76. The greater the distance from the first opening 77 (first blade 82) on the first inner sloped surface 86 becomes, the smaller the distance from the center axis P of the through-hole 76 becomes. Thus, the greater the distance becomes from the first opening 77 in the region of the through-hole 76 in which the first inner sloped surface 86 extends, the smaller the cross-sectional area substantially perpendicular to the extending direction of the through-hole 76 becomes. Also, the greater the distance becomes from the second opening 78 (second blade 84) on the second inner sloped surface 87, the smaller the distance becomes from the center axis P of the through-hole 76. Thus, the greater the distance becomes from the second opening 78 in the region of the through-hole 76 in which the second inner sloped surface 87 extends, the smaller the cross-sectional area substantially perpendicular to the extending direction of the through-hole 76 becomes. The inner extending surface 88 extends substantially parallel to the extending direction of the through-hole 76. Thus, in the region in the through-hole 76 in which the inner extending surface 88 extends, the cross-sectional area substantially perpendicular to the extending direction of the through-hole 76 is uniform or substantially uniform.

On the outer surface 70 of the treating portion 64, an outer relay surface 90 is provided. The outer relay surface 90 extends from the first blade 82 on the first outer surface 72 to the second blade 84 on the second outer surface 74 along the thickness direction of the treating portion 64. The outer relay surface 90 faces away from the center axis P of the through-hole 76 in radial direction of the through-hole 76. In the embodiment, the first blade 82 is formed at a boundary between the first inner sloped surface 86 and the outer relay surface 90, and the second blade 84 is formed at a boundary between the second inner sloped surface 87 and the outer relay surface 90. Also, in the embodiment, the outer relay surface 90 extends across a region from the first blade 82 to the second blade 84, substantially parallel to the thickness direction of the treating portion 64, that is, the extending direction of the through-hole 76.

The outer relay surface 90 includes a distal outer surface 91 facing the distal side in a direction along the center axis L. The distal outer surface 91 of the embodiment forms a distal end of the treating portion 64, that is, a distal end of the ultrasonic probe 56. The distal outer surface 91 of the embodiment is further a curved surface, and becomes arc-like or substantially arc-like in projection from each of the first outer surface 72 side and the second outer surface 74 side in the thickness direction of the treating portion 64. The outer relay surface 90 further includes a first lateral surface 93 facing one side (arrow W1 side) in width direction of the treating portion 64, and a second lateral surface 95 facing a side (arrow W2 side) opposite to the side to which the first lateral surface 93 is facing. The distal end of the first lateral surface 93 and the distal end of the second lateral surface 95 continue to the distal outer surface 91. Further, in the embodiment, each of the first lateral surface 93 and the second lateral surface 95 has a planar shape substantially parallel to the center axis L of the treating portion 64. Therefore, in projection from each of the first outer surface 72 side and the second outer surface 74 side in the thickness direction of the treating portion 64, each of the first lateral surface 93 and the second lateral surface 95 has the shape of a straight line substantially parallel to the extending direction of the treating portion 64. Also, the outer relay surface 90 of the embodiment which includes the distal outer surface 91 and the lateral surfaces 93 and 95 continues across the region from the first blade 82 of the first outer surface 72 to the second blade 84 of the second outer surface 74. Furthermore, the first lateral surface 93 and the second lateral surface 95 of the embodiment are substantially parallel to each other. Further, in the embodiment, the distance between a distal position E1 of the lateral surfaces 93 and 95 and the distal end of the treating portion 64 in the direction along the center axis L is preferably 1.5 mm or less. Here, the distal position E1 of the lateral surfaces 93 and 95 is the boundary between the distal outer surface 91 and the first lateral surface 93, as well as the boundary between the distal outer surface 91 and the second lateral surface 95.

In the embodiment, the opening width dimension of each of the first opening 77 and the second opening 78 in width direction (direction indicated by the arrows W1 and W2) of the treating portion 64 is maximum in the region in which the lateral surfaces 93 and 95 extend in the direction along the center axis L. In a region located on the proximal side with respect to a proximal position E2 of the lateral surfaces 93 and 95, the opening width dimension of the first opening 77 and the opening width dimension the second opening 78 decrease towards the proximal side. At the proximal end of the edge of the first opening 77, the opening width dimension of the first opening 77 is substantially zero, and at the proximal end of the edge of the second opening 78, the opening width dimension of the second opening 78 is substantially zero. Moreover, in the embodiment, the first blade 82 is formed across the entire region located on the distal side with respect to the proximal position E2 (proximal position E2 of the outer relay surface 90) of the lateral surfaces 93 and 95 in the edge of the first opening 77. Also, the second blade 84 is formed across the entire region located on the distal side with respect to the proximal position E2 (proximal position E2 of the outer relay surface 90) of the lateral surfaces 93 and 95 in the edge of the second opening 78.

Figure 5:
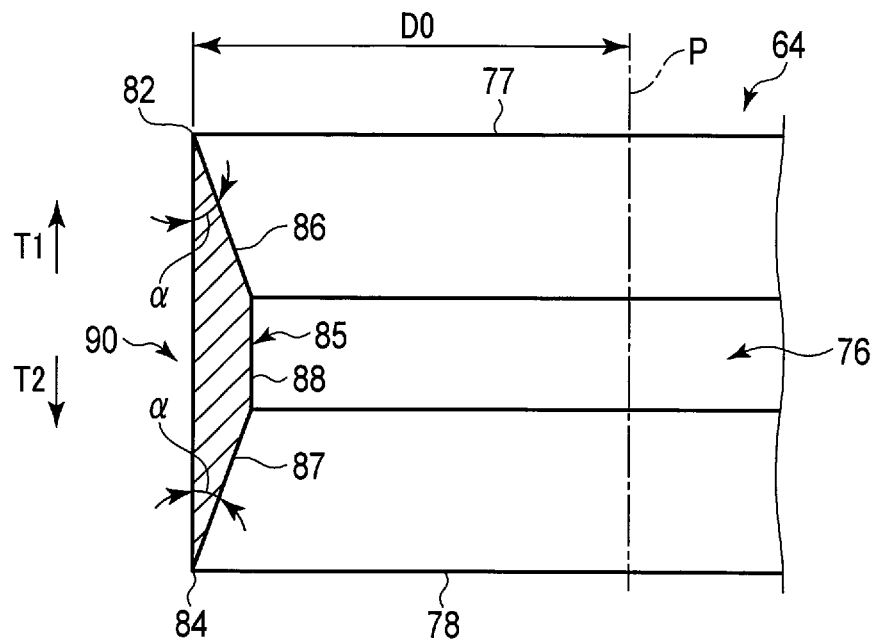
FIG. 5 is a cross-sectional view of the treating portion of an exemplary embodiment, schematically showing a cross section which passes through an outer relay surface and which is substantially perpendicular to a direction around a center axis of a through-hole.

FIG. 5 is a view showing a cross section of the treating portion 64 which passes through the outer relay surface 90 (blades 82 and 84) and which is substantially perpendicular to the direction around the center axis P of the through-hole 76. As shown in FIG. 5, in the cross section substantially perpendicular to the direction around the center axis P of the through-hole 76, the distance from the center axis P of the through-hole 76 to the first blade 82 and the distance from the center axis P of the through-hole 76 to the second blade 84 are the same. Here, the distance from the center axis P to the first blade 82 and the distance from the center axis P to the second blade 84 are defined as reference distance D0. In a cross section shown in FIG. 5, the distance from the center axis P of the through-hole 76 to the outer relay surface 90 is substantially the same as the reference distance D0 across the region from the first blade 82 to the second blade 84. Thus, in the cross section of FIG. 5, the distance from the center axis P of the through-hole 76 to the outer relay surface 90 across the region from the first blade 82 to the second blade 84 of the second outer surface 74 is kept equal to or less than the reference distance D0 from the center axis P to the first blade 82. Also, in the cross section of FIG. 5, the distance from the center axis P to the outer relay surface 90 is maximum at each of the first blade 82 and the second blade 84.

In the embodiment, not only in the cross section of FIG. 5 but any cross section which passes through the outer relay surface 90 (blades 82 and 84) and which is substantially perpendicular to the direction around the center axis P of the through-hole 76, the distance from the center axis P of the through-hole 76 to the outer relay surface 90 across the region from the first blade 82 to the second blade 84 is substantially equal to the reference distance which is the distance from the center axis P to the first blade 82. Therefore, in any cross section which passes through the outer relay surface 90 and is substantially perpendicular to the direction around the center axis P of the through-hole 76, the distance from the center axis P of the through-hole 76 to the outer relay surface 90 across the region from the first blade 82 to the second blade 84 of the second outer surface 74 is kept equal to or less than the reference distance from the center axis P to the first blade 82 (second blade 84). Moreover, in any cross section which passes through the outer relay surface 90 and is substantially perpendicular to the direction around the center axis P of the through-hole 76, the distance from the center axis P to the outer relay surface 90 is maximum at each of the first blade 82 and the second blade 84.

The angle formed by each of the first inner sloped surface (first blade-forming surface) 86 and the second inner sloped surface (second blade-forming surface) 87 with respect to the direction along the center axis P is defined as the inner protrusion angle $\alpha$, and the angle formed by the outer relay surface 90 with respect to the direction along the center axis P is defined as the outer protrusion angle $\beta$. Each of the inner protrusion angle $\alpha$ and the outer protrusion angle $\beta$ is a parameter set within a range larger than $-90°$ but smaller than $90°$. The inner protrusion angle $\alpha$ is a parameter indicating the extent of protrusion of the inner relay surface 85 towards the side approximating the center axis P with respect to the first blade 82 and the second blade 84. As the inner protrusion angle $\alpha$ increases, the extent of protrusion of the inner relay surface 85 towards the side approximating the center axis P with respect to the first blade 82 and the second blade 84 increases. If the inner relay surface 85 is concave towards the side away from the center axis P with respect to the first blade 82 and the second blade 84, the inner protrusion angle $\alpha$ takes a negative value. The outer protrusion angle $\beta$ is a parameter indicating the extent of protrusion of the outer relay surface 90 towards the side away from the center axis P with respect to the first blade 82 and the second blade 84. As the outer protrusion angle $\beta$ increases, the extent of protrusion of the outer relay surface 90 towards the side away from the center axis P with respect to the first blade 82 and the second blade 84 increases. If the outer relay surface 90 is concave towards the center axis P with respect to the first blade 82 and the second blade 84, the outer projection angle $\beta$ takes a negative value.

Since the treating portion 64 of the embodiment is formed as mentioned, the inner protrusion angle $\alpha$ takes a positive value. Also, as the outer relay surface 90 is substantially parallel to the center axis P, the outer protrusion angle $\beta$ is zero or substantially zero, which is not shown in FIG. 5. Consequently, in the embodiment, the outer relay surface 90 does not protrude towards the side away from the center axis P with respect to the first blade 82 and the second blade 84.

Next, functions and effects of the treatment system 1 of the embodiment will be described. Here, treatment for excising cartilage mainly in the knee joint 100 will be described. When performing the treatment using the treatment system 1, the arthroscope 12 is inserted into the joint cavity 101 via the first portal 102, and the ultrasonic treatment instrument 42 of the treatment unit 22 is inserted into the joint cavity 101 via the second portal 104. The treatment using the ultrasonic treatment instrument 42 is performed while observing the subject with the arthroscope 12. It should be noted that it is preferable during the treatment that the supply and discharge of perfusion fluid into or from the joint cavity 101 with the perfusion device 6 be performed as mentioned.

The knee joint 100 is mainly constituted of a femur 112 (see FIG. 1), a tibia 114 (see FIG. 1), a fibia (not shown), and a patella (not shown). The knee joint 100 has a cartilage 112A on the surface of the femur 112 in a region facing the tibia 114, and the femur 112 includes a subchondral bone (not shown) forming the surface, and a cancellous bone 112B (see FIGS. 9, 11) forming the interior. Moreover, the knee joint 100 exhibits a cartilage 114A on the surface of the tibia 114 in a region facing the femur 112. The knee joint 100 further has cartilage (not shown) on the surface of the patella in a region facing the femur 112. In the embodiment, any of the aforementioned cartilages in the joint cavity 101 is abraded and excised by the treating portion 64 of the treatment unit 22. As an example, when cartilage degeneration occurs in part of the aforementioned cartilages, the cartilage in the degenerated region is excised.

When abrading cartilage, the first blade 82 or the second blade 84 of the treating portion 64 is brought into contact with the cartilage as the treatment object. While the first blade 82 or the second blade 84 is in contact with the cartilage, an input operation using the operating member 26 is performed to output electric energy from the controller 24 to the transducer 48. In this manner, the transducer 48 generates ultrasonic vibration which is then transmitted via the ultrasonic probe 56 to the treating portion 64. While ultrasonic vibration is transmitted to the treating portion 64, the vibrating body 50 including the transducer 48 and the ultrasonic probe 56 vibrates at any resonance frequency within the predetermined frequency range. By causing the treating portion 64 to vibrate while the first blade 82 or second blade 84 is in contact with cartilage, the cartilage is abraded and excised. At this point, while maintaining the contact of the first blade 82 or the second blade 84 with the cartilage, the treating portion 64 is moved inside the joint cavity 101 to abrade and excise the cartilage. With a treating portion 64 having the curette shape according to the embodiment, the first blade 82 or the second blade 84 is brought into contact with the cartilage, and the cartilage is excised while the treating portion 64 is moved along the extending direction of the through-hole 76, that is, along the thickness direction of the treating portion 64. Here, while the vibrating body 50 vibrates at any resonance frequency within the predetermined frequency range, an anti-node is generated at the distal end of the treating portion 64.

Figure 6:
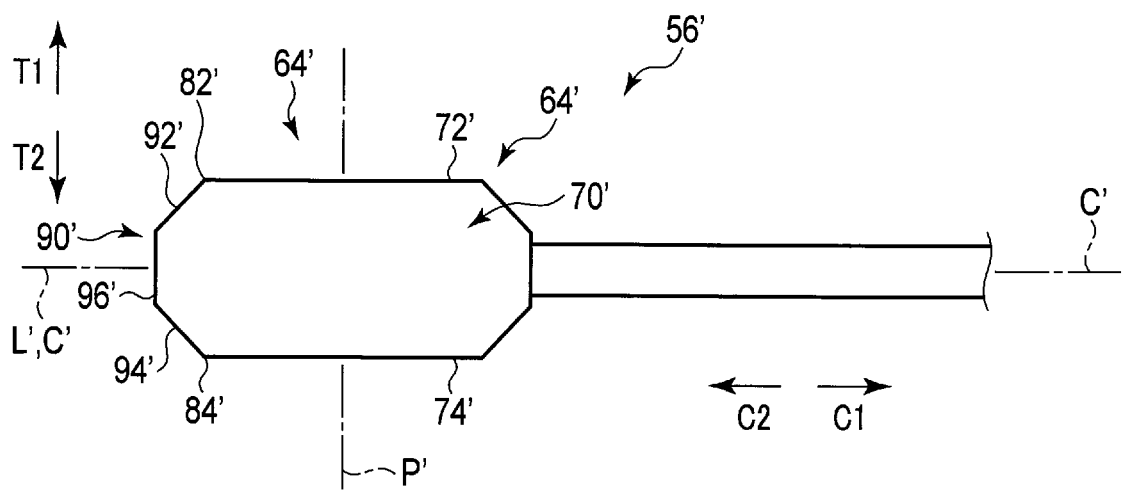
FIG. 6 is a schematic view showing the treating portion of the ultrasonic probe according to a comparative example.
Figure 7:
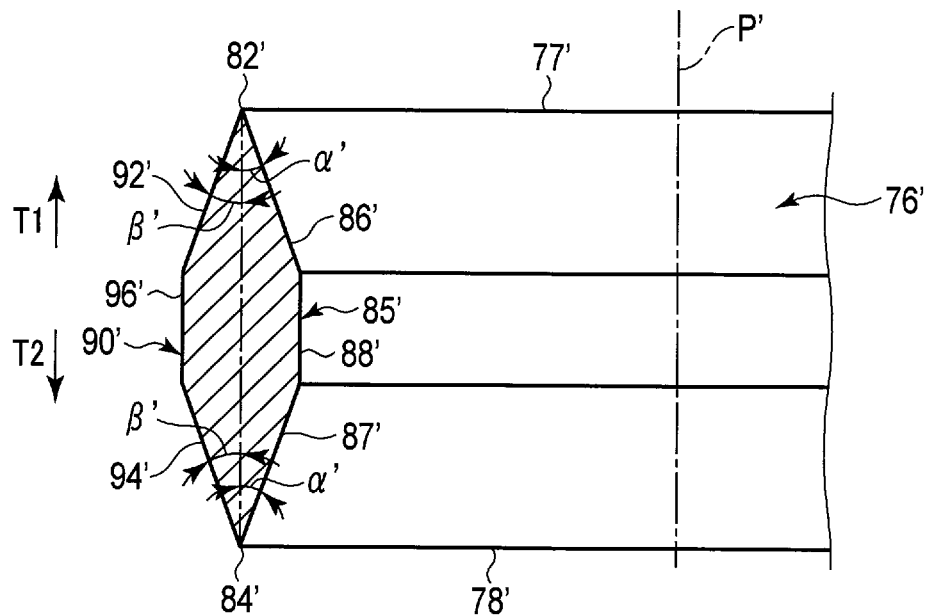
FIG. 7 is a cross-sectional view of the treating portion of the comparative example, schematically showing a cross section which passed through an outer relay surface and which is substantially perpendicular to a direction around a center axis of a through-hole.

An ultrasonic probe 56' shown in FIGS. 6 and 7 serves as a comparative example. In the ultrasonic probe 56' of the comparative example, a treating portion 64' has, similar to the embodiment, a first outer surface 72' and a second outer surface 74', and a through-hole 76' is formed extending through the first outer surface 72' to the second outer surface 74'. Moreover, as in the embodiment, on the first outer surface 72', a first blade 82' is formed along the edge of the first opening 77' of the through-hole 76', and on the second outer surface 74', a second blade 84' is formed along the edge of a second opening 78' of the through-hole 76'. As in the embodiment, the treating portion 64' includes an inner relay surface 85' and an outer relay surface 90', and the inner relay surface 85' includes inner sloped surfaces 86' and 87' and an inner extending surface 88'. Thus, the inner relay surface 85' in the comparative example also protrudes towards a center axis P' of the through-hole 76' with respect to the first blade 82' and the second blade 84', and an inner protrusion angle α' takes a positive value. It should be noted that FIG. 6 shows a state of the treating portion 64' viewed from one side in width direction, and FIG. 7 shows a cross section which passes through the outer relay surface 90' (blades 82', 84') in the treating portion 64' and is substantially perpendicular to a direction around the center axis P' of the through-hole 76'.

In the ultrasonic probe 56' of the comparative example, the outer relay surface 90' includes a first outer sloped surface 92' extending from the first blade 82' to the second outer surface 74' side, a second outer sloped surface 94' extending from the second blade 84' to the first outer surface 72' side, and an outer extending surface 96' continuing between the first outer sloped surface 92' and the second outer sloped surface 94' in thickness direction of the treating portion 64'. Each of the outer sloped surfaces 92' and 94' is sloped with respect to the thickness direction of the treating portion 64', that is, the extending direction of the through-hole 76'. The greater the distance becomes from the first blade 82' on the first outer sloped surface 92', the greater the distance from the center axis P' of the through-hole 76' becomes. Also, the greater the distance becomes from the center axis P' in the second outer sloped surface 94', the greater the distance from the second blade 84' becomes. The outer extending surface 96' extends substantially parallel to the extending direction of the through-hole 76'.

Since the comparative example has the mentioned configuration, in any cross section which passes through the outer relay surface 90' (blades 82', 84') (including the cross section of FIG. 7) and is substantially perpendicular to the direction around the center axis P' of the through-hole 76', in at least a part between the first blade 82' and the second blade 84', the distance from the center axis P' of the through-hole 76' to the outer relay surface 90' is larger than a reference distance from the center axis P' to the first blade 82' (second blade 84'). As a result, in any cross section which passes through the outer relay surface 90' and is substantially perpendicular to the direction around the center axis P', at a position different from the first blade 82' and the second blade 84', the distance from the center axis P' to the outer relay surface 90' is maximum. As an example, on the outer extending surface 96' being a position different from the first blade 82' and the second blade 84', the distance from the center axis P' to the outer relay surface 90' is maximum.

Also, in the comparative example, the outer protrusion angle β', which is the angle formed by each of the first outer sloped surface 92' and the second outer sloped surface 94' with respect to the direction along the center axis P', is a positive value. Therefore, in the comparative example, the outer relay surface 90' protrudes to the side away from the center axis P' with respect to the first blade 82' and the second blade 84'.

When excising cartilage (for example, the portion denoted by the reference numeral 112A) using the ultrasonic probe 56' of the comparative example or the ultrasonic probe 56 of the embodiment, first, the blade (82; 84; 82'; 84') is brought into contact with the cartilage (112A), and the treating portion (64; 64') caused by the ultrasonic vibration to vibrate is moved substantially parallel to the surface of the cartilage (112A). In this manner, the treating portion (64; 64') excises the cartilage (112A) along the direction of movement of the treating portion (64; 64') substantially parallel to the surface of the cartilage (112A). Here, the operation by which the treating portion (64; 64') excises the cartilage (112A) along the direction of movement is referred to as "abrasion".

Figure 8:
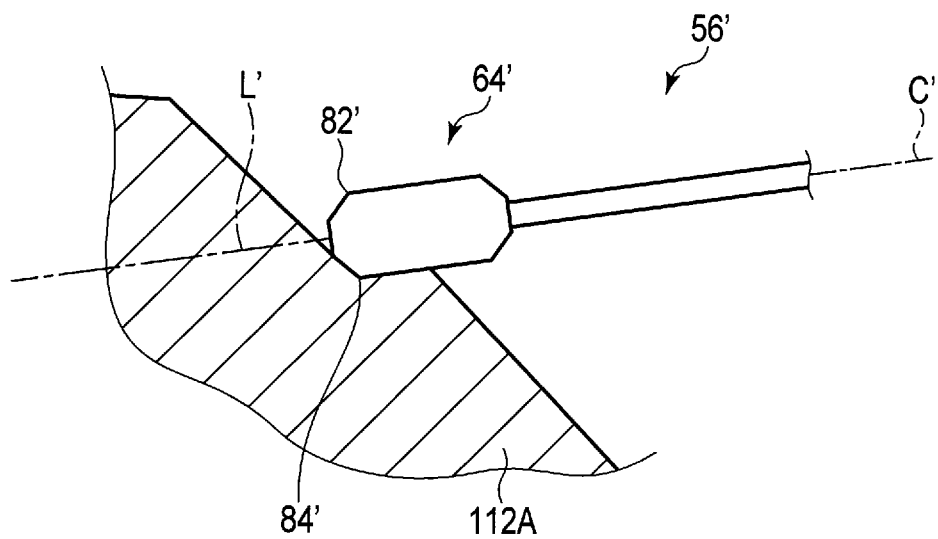
FIG. 8 is a schematic view showing an example of a state in which the treating portion of the ultrasonic probe of the comparative example performs abrasion of cartilage.
Figure 9:
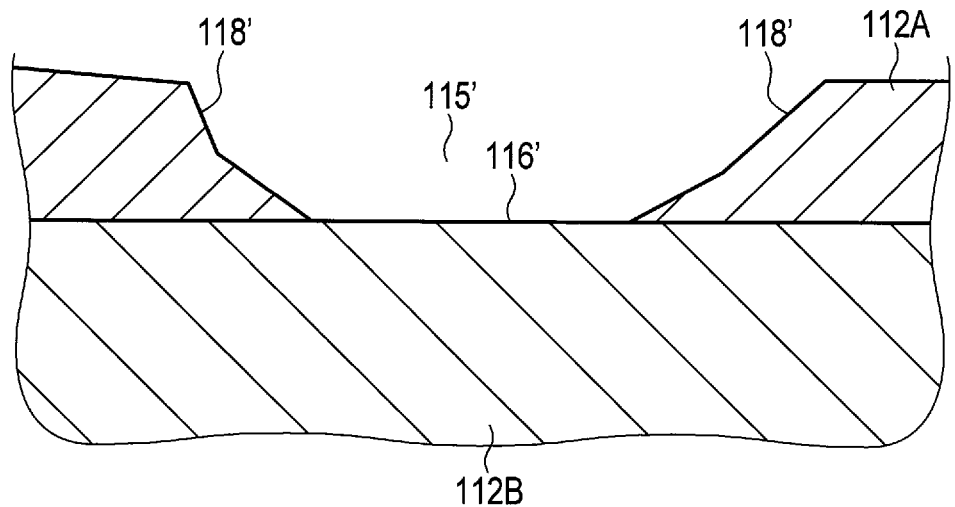
FIG. 9 is a schematic view showing an example of an excised portion from which cartilage has been excised per a single abrasion using the treating portion of the ultrasonic probe of the comparative example.

FIG. 8 shows an example of a state in which the treating portion 64' of the ultrasonic probe 56' of the comparative example performs abrasion of cartilage (112A) while moving substantially parallel to the surface of the cartilage (112A). FIG. 9 shows an example of an excised portion 115' from which cartilage (112A) has been excised per a single abrasion using the treating portion 64' of the ultrasonic probe 56' of the comparative example. It should be noted that FIG. 9 shows the excised portion 115' during abrasion in a cross section substantially parallel to the direction of movement of the treating portion 64'. As mentioned, in the ultrasonic probe 56' of the comparative example, in any cross section substantially perpendicular to the direction around the center axis P' of the through-hole 76', in at least a part between the first blade 82' and the second blade 84', the distance from the center axis P' of the through-hole 76' to the outer relay surface 90' is greater than the reference distance from the center axis P' to the first blade 82' (second blade 84'). Thus, the outer relay surface 90' protrudes to the side away from the center axis P' with respect to the first blade 82' and the second blade 84'. In this manner, when performing abrasion of the cartilage (112A) using the ultrasonic probe 56', the outer relay surface 90' interferes with the cartilage (112A) before the first blade 82' or the second blade 84' comes into contact with the cartilage. Especially the protruding portion with respect to the blades 82', 84' on the outer relay surface 90' can easily interfere with the cartilage (112A). As the outer relay surface 90' interferes with the cartilage (112A) before the blade (82' or 84') comes into contact, the angle between the bottom surface 116' and the lateral surface 118' in the excised portion 115' where the cartilage (112A) was excised per the single abrasion can easily become an obtuse angle greater than a right angle, and the lateral surface 118' cannot easily become perpendicular to the bottom surface 116', as shown in FIGS. 8 and 9.

Figure 10:
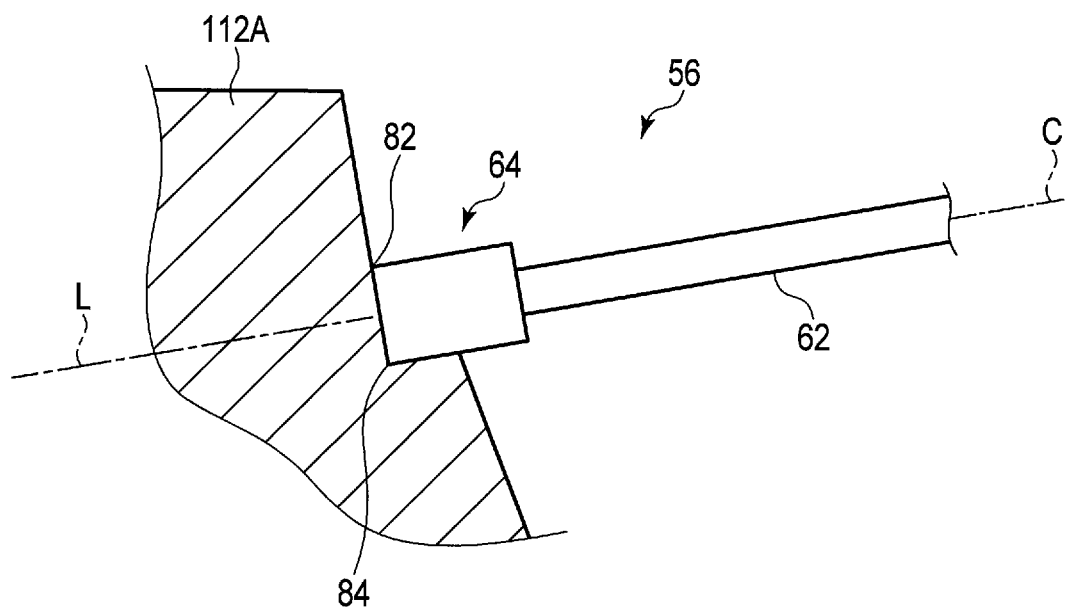
FIG. 10 is a schematic view showing an example state in which the treating portion of the ultrasonic probe of an exemplary embodiment performs abrasion of cartilage.
Figure 11:
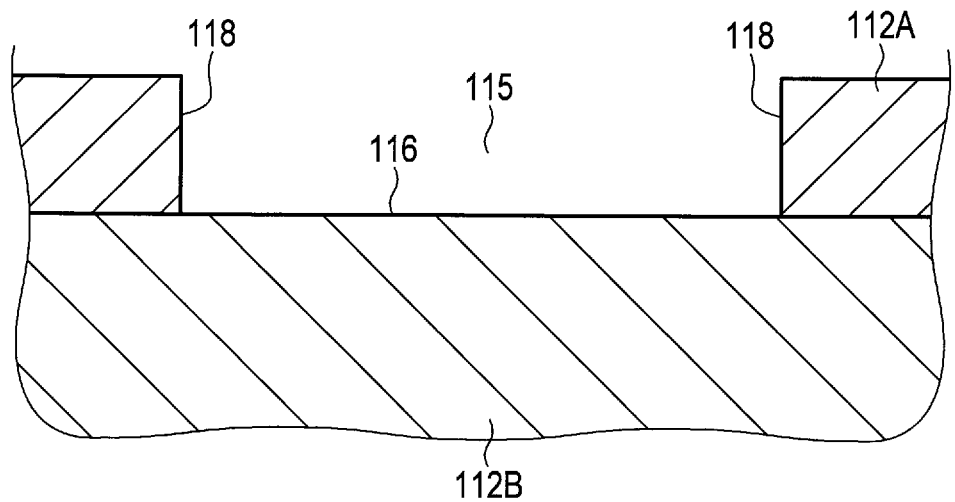
FIG. 11 is a schematic view showing an example of an excised portion from which cartilage has been excised per a single abrasion using the treating portion of the ultrasonic probe of an exemplary embodiment.

FIG. 10 shows an example of a state in which the treating portion 64 of the ultrasonic probe 56 of the embodiment performs abrasion of cartilage (112A) while moving substantially parallel to the surface of the cartilage (112A). FIG. 11 shows an example of the excised portion 115 from which the cartilage (112A) has been excised per a single abrasion using the treating portion 64 of the ultrasonic probe 56 according to the embodiment. It should be noted that FIG. 11 shows the excised portion 115 during abrasion in a cross section substantially parallel to the direction of movement of the treating portion 64. As mentioned, in the ultrasonic probe 56 of the embodiment, in each cross section which passes through the outer relay surface 90 (blades 82 and 84) and is substantially perpendicular to the direction around the center axis P of the through-hole 76, the distance from the center axis P of the through-hole 76 to the outer relay surface 90 across the region from the first blade 82 to the second blade 84 of the second outer surface 74 is kept equal to or less than the reference distance from the center axis P to the first blade 82 (second blade 84). The outer relay surface 90 does not protrude towards the side away from the center axis P with respect to the first blade 82 and the second blade 84. In this manner, it is effectively prevented that, when abrasion of the cartilage (112A) is performed using the ultrasonic probe 56, the outer relaying surface 90 contacts the cartilage (112A) before the first blade 82 or the second blade 84 comes into contact with the cartilage (112A). By preventing interference of the outer relay surface 90 with the cartilage (112A) before the blade (82 or 84) comes into contact with the cartilage (112A), the angle between the bottom surface 116 and the lateral surface 118 in the excised portion 115 from which cartilage (112A) was excised by the single abrasion can easily become a substantially right angle, and the lateral surface 118 can easily become perpendicular to the bottom surface 116, as shown in FIGS. 10 and 11. Since the bottom surface 116 and the lateral surface 118 are substantially perpendicular to each other in the excised portion 115 of the cartilage (112A), a medical solution or the like for the treatment can be accumulated in the excised portion 115 of the cartilage (112A) in an easy and reliable fashion. Performing bone fenestration (the microfracture method) under arthroscopy forms perforations in the subchondral bone and promotes the regeneration of cartilage by the blood and the bone marrow fluid. Accumulating more blood and bone marrow fluid in the excised portion 115 contributes to the promotion of the regeneration of the cartilage tissue.

Figure 12:
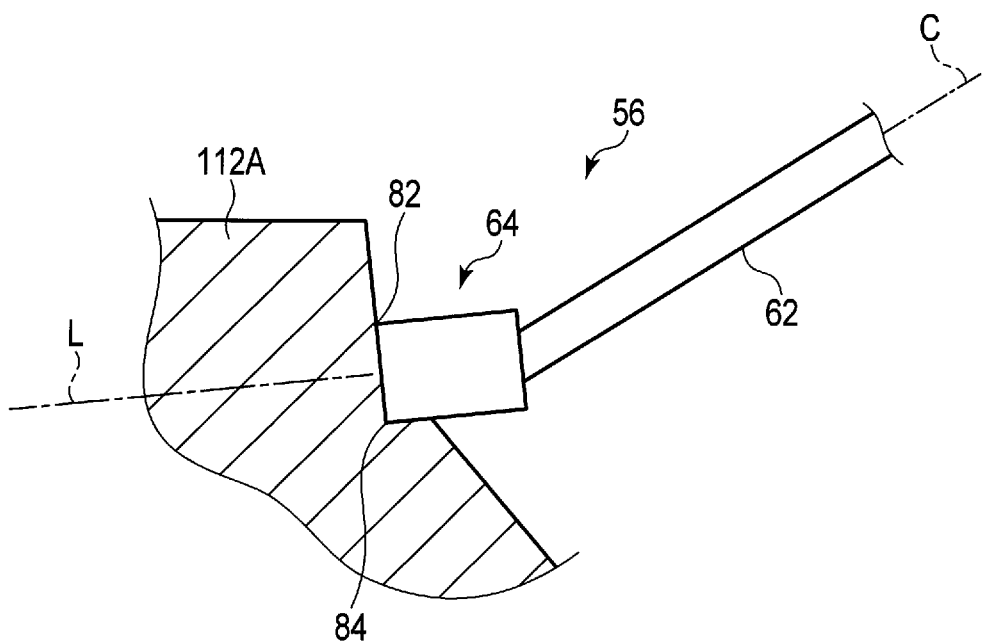
FIG. 12 is a schematic view showing an example state in which the treating portion of the ultrasonic probe of an exemplary embodiment performs abrasion of cartilage, the treating portion being bent or curved with respect to a probe main body.
Figure 13:
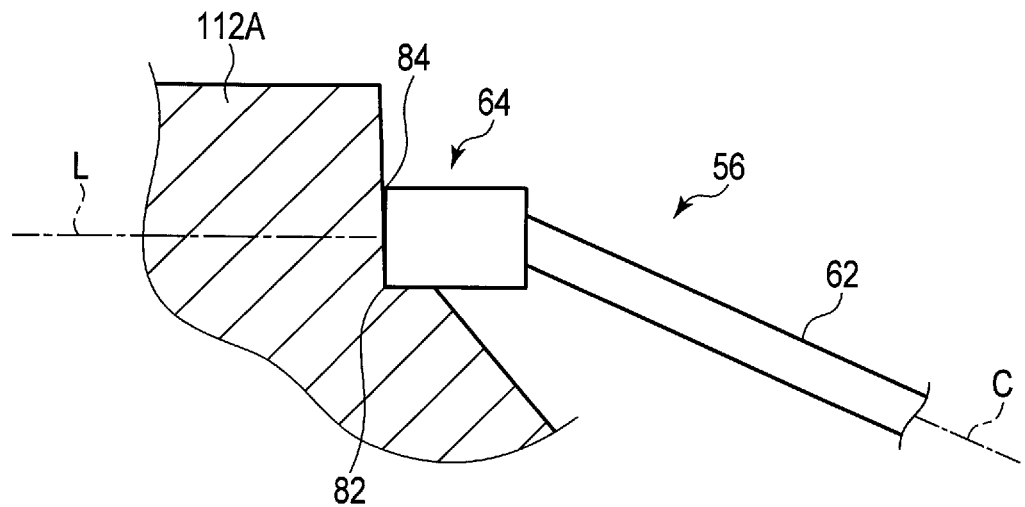
FIG. 13 is a schematic view showing an example state in which the treating portion of the ultrasonic probe of an exemplary embodiment performs abrasion of cartilage, the treating portion being bent or curved with respect to a probe main body.

FIGS. 12 and 13 are views showing an example state in which the treating portion 64 performs excision of cartilage (112A) using the ultrasonic probe 56 with the treating portion 64 bent or curved with respect to the probe main body 62. In FIGS. 12 and 13, the sites at which abrasion of cartilage is performed are different from each other. By bending or curving the treating portion 64 with respect to the probe main body 62, even when the cartilage as the treatment object is excised at sites having a narrow approach angle, the treating portion 64 can reliably be brought into contact with the cartilage while the extending direction of the treating portion 64 (i.e. center axis L) is perpendicular to the surface of the cartilage (112A), as shown in FIGS. 12 and 13. In this manner, even at a narrow approach angle, the abrasion of cartilage can easily and reliably be performed while the extending direction of the treating portion 64 (i.e. center axis L) is perpendicular to the surface of the cartilage (112A).

Further, in the embodiment, the first blade 82 is provided on the first outer surface 72 and the second blade 84 is provided on the second outer surface 74. That is, the blades (82 and 84) are provided on the outer surfaces (72, 74) on both sides in the thickness direction of the treating portion 64. Therefore, by configuring the treating portion 64 to bend or curve with respect to the probe main body 62, the blades (82 and 84) can be brought into contact with various sites in the cartilage (112A) in the joint cavity 101, thus making it possible to perform the abrasion of cartilage (112A) as the treatment object at various places. As an example, when the site shown in FIG. 12 is the treatment object, the second blade 84 is brought into contact with the cartilage (112A) to excise cartilage. When the site shown in FIG. 13 is the treatment object, the first blade 82 is brought into contact with the cartilage (112A) to excise the cartilage.

It should be noted that in the above exemplary embodiment, in each cross section passing through the outer relay surface 90 (blades 82 and 84) and being substantially perpendicular to the direction around the center axis P of the through-hole 76, the distance from the center axis P of the through-hole 76 to the outer relay surface 90 across the region from the first blade 82 to the second blade 84 is substantially equal to the reference distance being the distance from the center axis P to the first blade 82. However, it is not limited to this. As an example, in an exemplary embodiment shown in FIG. 14, the outer relay surface 90 includes the first outer sloped surface 92 extending from the first blade 82 to the second outer surface 74 side, the second outer sloped surface 94 extending from the second blade 84 to the first outer surface 72 side, and the outer extending surface 96 continuing between the first outer sloped surface 92 and the second outer sloped surface 94 in the thickness direction of the treating portion 64. Each of the outer sloped surfaces 92 and 94 is sloped with respect to the thickness direction of the treating portion 64, that is, the extending direction of the through-hole 76. The greater the distance becomes from the first blade 82 on the first outer sloped surface 92, the smaller the distance becomes from the center axis P of the through-hole 76. Similarly, the greater the distance becomes from the second blade 84 on the second outer sloped surface 94, the smaller the distance becomes from the center axis P. The outer extending surface 96 extends substantially parallel to the extending direction of the through-hole 76. In another exemplary embodiment, the outer relay surface 90 may not have the outer extending surface 96, and the outer relay surface 90 may be composed of the first outer sloped surface 92 and the second outer sloped surface 94.

Since the present embodiment has the mentioned configuration, in this embodiment as well, in each cross section passing through the outer relay surface 90 and being substantially perpendicular to the direction around the center axis P of the through-hole 76, the distance from the center axis P of the through-hole 76 to the outer relay surface 90 across the region from the first blade 82 to the second blade 84 of the second outer surface 74 is kept equal to or less than the reference distance from the center axis P to the first blade 82 (second blade 84). Moreover, in any cross section passing through the outer relay surface 90 and being substantially perpendicular to the direction around the center axis P of the through-hole 76, the distance from the center axis P to the outer relay surface 90 is maximum at each of the first blade 82 and the second blade 84.

Moreover, since the present embodiment has the mentioned configuration, in this embodiment, the outer protrusion angle R, which is the angle formed by each of the first outer sloped surface 92 and the second outer sloped surface 94 with respect to the direction along the center axis P, takes a negative value. Therefore, in this embodiment, the outer relay surface 90 is concave towards the center axis P with respect to the first blade 82 and the second blade 84. Consequently, in this embodiment as well, the outer relay surface 90 does not protrude towards the side away from the center axis P with respect to the first blade 82 and the second blade 84. It should also be noted that in this embodiment, the absolute value of the inner protrusion angle α, which is the angle formed by each of the first inner sloped surface 86 and the second inner sloped surface 87 with respect to the direction along the center axis P, is larger than the absolute value of the outer protrusion angle β.

Figure 15:
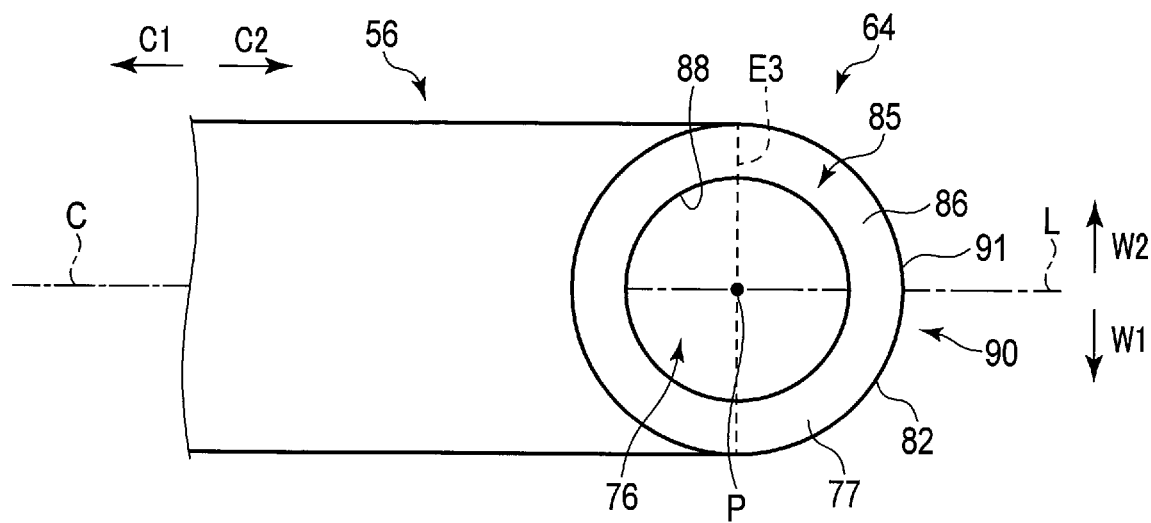
FIG. 15 is a schematic view showing a treating portion of an ultrasonic probe according to an exemplary embodiment.

Also, neither the cross sectional shape substantially perpendicular to the center axis P of the through-hole 76 nor the shape of the region surrounded by each of the edge of the first opening 77 and the edge of the second opening 78 are limited to the aforementioned substantially pentagonal shape. In another exemplary embodiment shown in FIG. 15, the cross-sectional shape substantially perpendicular to the center axis P of the through-hole 76 and the shape of the region surrounded by each of the edge of the first opening 77 and the edge of the second opening 78 are substantially circular. In this case, the first lateral surface 93 and the second lateral surface 95 parallel to the center axis L are not provided, and the outer relay surface 90 is formed only from the distal outer surface 91. In this embodiment, the outer relay surface 90 (distal outer surface 91) in the projection from the first outer surface 72 side and the second outer surface 74 side in the thickness direction of the treating portion 64 forms a semicircular arc centered on the center axis P of the through-hole 76. In this case, a proximal end position E3 of the distal outer surface 91 (proximal end position E3 of the outer relay surface 90) is substantially aligned with the center axis P of the through-hole 76 in a direction along the center axis L. In another exemplary embodiment, the cross-sectional shape substantially perpendicular to the center axis P of the through-hole 76 and the shape of the region surrounded by each of the edge of the first opening 77 and the edge of the second opening 78 have a polygonal shape other than a pentagonal shape, that is, for example, a substantially quadrangular shape.

Although in the aforementioned embodiment, the first blade 82 is provided on the first outer surface 72, and the second blade 84 is provided on the second outer surface 74 facing the side opposite to the side where the first outer surface 72 faces, it is not limited to this. In another exemplary embodiment, only the first blade 82 may be provided, and no blade may be formed on the second outer surface 74. In this embodiment as well, the through-hole 76 is provided that penetrates from the first outer surface 72 to the second outer surface 74. The inner relay surface 85 extends from the first opening 77 to the second opening 78, and the outer relay surface 90 extends from the first blade 82 to the second outer surface 74. In this embodiment as well, in each cross section perpendicular to the direction around the center axis P of the through-hole 76, the distance from the center axis P of the through-hole 76 to the outer relay surface 90 across the region from the first blade 82 to the second outer surface 74 is kept equal to or less than the reference distance from the center axis P to the first blade 82. That is, in any cross section passing through the outer relay surface 90 and being substantially perpendicular to the direction around the center axis P of the through-hole 76, the distance from the center axis P to the outer relay surface 90 at the first blade 82 is maximum.

Next, another exemplary embodiment will be described with reference to FIGS. 16 to 18. Differences between this embodiment and the above-discussed exemplary embodiments are described below. Parts that are same as those of the above exemplary embodiments will be denoted by same reference numerals, and descriptions thereof will be omitted.

Figure 16:
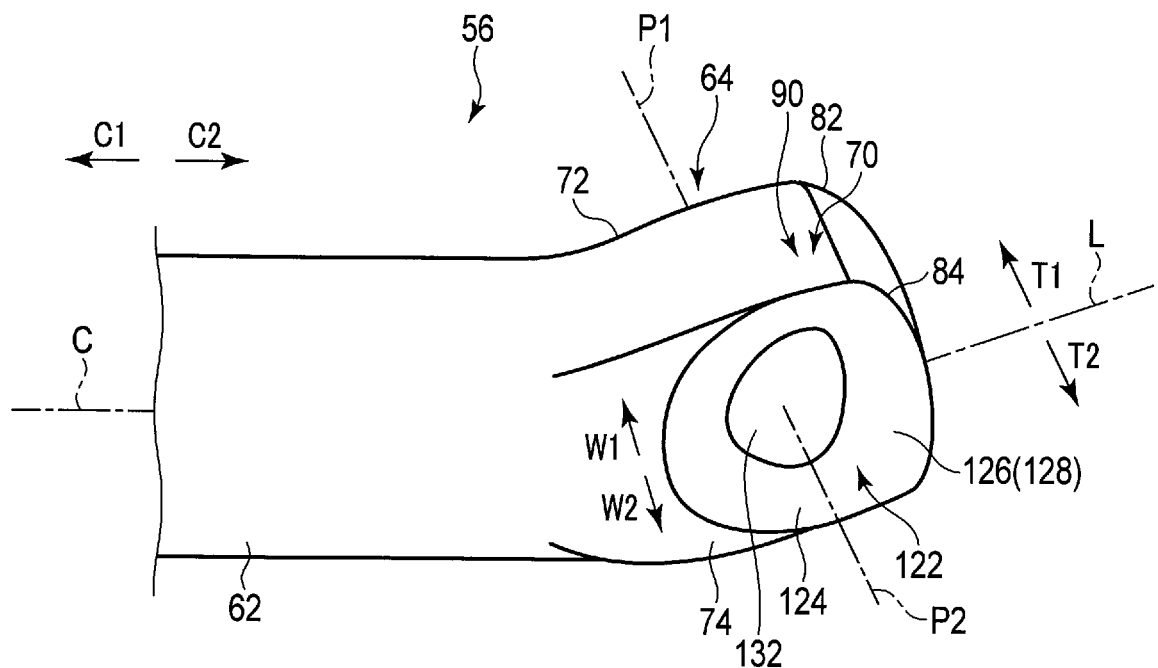
FIG. 16 is a perspective view schematically showing a configuration of a treating portion of an ultrasonic treatment instrument according to an exemplary embodiment.
Figure 17:
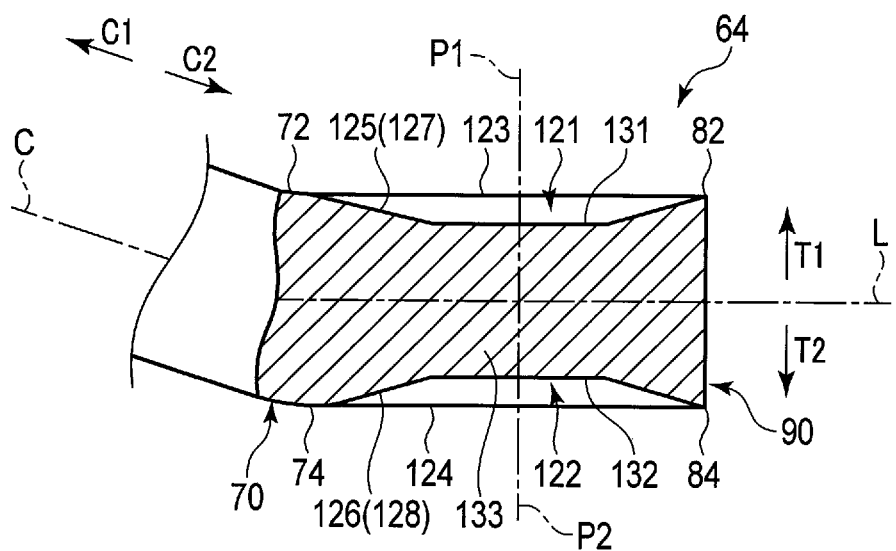
FIG. 17 is a cross-sectional view schematically showing the configuration of the treating portion of the ultrasonic treatment instrument according to an exemplary embodiment.

FIGS. 16 and 17 show a configuration of the treating portion 64 according to the second embodiment. FIG. 17 shows the treating portion 64 in a cross section substantially perpendicular to the width direction (direction indicated by the arrows W1 and W2). As shown in FIGS. 16 and 17, in this embodiment as well, the outer surface 70 of the treating portion 64 includes the aforementioned first outer surface 72 and the second outer surface 74. However, in this embodiment, the through-hole 76 is not provided in the treating portion 64. Instead, in the embodiment, a first concave portion 121 concave towards the second outer surface 74 side is provided on the first outer surface 72, and a second concave portion 122 concave towards the first outer surface 72 side is provided on the second outer surface 74. The first concave portion 121 opens at a first opening 123 on the first outer surface 72, and the second concave portion 122 opens at a second opening 124 on the second outer surface 74.

The first concave portion 121 extends from the first opening 123 to the second outer surface 74 side along a center axis P1, and the second concave portion 122 extends from the second opening 124 to the first outer surface 72 side along a center axis P2. In this embodiment, the center axis P1 of the first concave portion 121 and the center axis P2 of the second concave portion 122 are substantially coaxial with each other. Also, the concave portions 121 and 122 are substantially coaxial with each other. In addition, the concaving direction of each of the concave portions 121 and 122, that is, the direction along each of the central axes P1 and P2 is substantially parallel to the thickness direction of the treating portion 64 (direction indicated by the arrows T1 and T2). Furthermore, on the first outer surface 72, the first blade 82 is formed along an edge of the first opening 123, and on the second outer surface 74, the second blade 84 is formed along an edge of the second opening 124. The first blade 82 extends along a direction around the center axis P1 of the first concave portion 121, and the second blade 84 extends along a direction around the center axis P2 of the second concave portion 122. It should be noted that the cross sectional shape substantially perpendicular to the center axis P1 of the first concave portion 121 and the shape of the region surrounded by the edge of the first opening 123 may be polygonal, e.g. substantially pentagonal, or substantially circular. Similarly, the cross-sectional shape substantially perpendicular to the center axis P2 of the second concave portion 122 and the shape of the region surrounded by the edge of the second opening 124 may be polygonal, e.g. substantially pentagonal, or substantially circular.

The treating portion 64 includes a first inner relay surface 125 forming a lateral surface (outer edge) of the first concave portion 121, and a second inner relay surface 126 forming a lateral surface (outer edge) of the second concave portion 122. The first inner relay surface 125 is formed, for example, annularly around the center axis P1 of the first concave portion 121, and the second inner relay surface 126 is formed, for example, annularly around the center axis P2 of the second concave portion 122. Also, the first concave portion 121 has a (first) bottom surface 131, and the second concave portion 122 has a (second) bottom surface 132. In this embodiment, each of the bottom surfaces 131 and 132 has a planar shape, but in an embodiment, each of the bottom surfaces 131 and 132 may have a curved shape. Between the bottom surfaces 131 and 132 in the thickness direction of the treating portion 64, a wall portion 133 is provided. The wall portion 133 isolates the first concave portion 121 from the second concave portion 122. Accordingly, the concave portions 121 and 122 do not communicate with each other. The first inner relay surface 125 extends from the first opening 123 of the first outer surface 72 to the bottom surface 131 along the thickness direction of the treating portion 64. Also, the first concave portion 121 is surrounded by the first inner relay surface 125, and the first inner relay surface 125 faces the side approximating the center axis P1 of the first concave portion 121 in radial direction of the first concave portion 121. Similarly, the second inner relay surface 126 extends from the second opening 124 of the second outer surface 74 to the bottom surface 132 along the thickness direction of the treating portion 64. Also, the second concave portion 122 is surrounded by the second inner relay surface 126, and the second inner relay surface 126 faces the side approximating the center axis P2 of the second concave portion 122 in radial direction of the second concave portion 122.

The first inner relay surface 125 includes a first inner sloped surface (first blade-forming surface) 127 extending from the first opening 123 toward the bottom surface 131, and the second inner relay surface 126 includes a second inner sloped surface (second blade-forming surface) 128 extending from the second opening 124 toward the bottom surface 132. Each of the first inner sloped surface 127 and the second inner sloped surface 128 is sloped to the thickness direction of the treating portion 64, that is, the direction along each of the center axis P1 of the first concave portion 121 and the center axis P2 of the second concave portion 122.

On the first inner sloped surface 127, the greater the distance becomes from the first opening 123 (first blade 82), the smaller the distance becomes from the center axis P1 of the first concave portion 121 (center axis P2 of the second concave portion 122). Therefore, in the first concave portion 121, in the region in which the first inner sloped surface 127 extends, the cross-sectional area substantially perpendicular to the center axis P1 of the first concave portion 121 decreases as the distance from the first opening 123 increases. Also, on the second inner sloped surface 128, the distance from the center axis P2 of the second concave portion 122 (center axis P1 of the first concave portion 121) decreases as the distance from the second opening 124 (the second blade 84) increases. Therefore, in the second concave portion 122, in the region in which the second inner sloped surface 128 extends, the cross-sectional area substantially perpendicular to the center axis P2 of the second concave portion 122 decreases as the distance from the second opening 124 increases. It should be noted that in this embodiment, the first inner sloped surface 127 continues from the first opening 123 to the bottom surface 131, and the entire first inner relay surface 125 is the first inner sloped surface 127. Similarly, the second inner sloped surface 128 continues from the second opening 124 to the bottom surface 132, and the entire second inner relay surface 126 is the second inner sloped surface 128.

In this embodiment, as in the ones before, the outer relay surface 90 is provided on the outer surface 70 of the treating portion 64. Also, the outer relay surface 90 extends from the first blade 82 of the first outer surface 72 to the second blade 84 of the second outer surface 74 along the thickness direction of the treating portion 64, and faces away from the center axis P1 of the first concave portion 121 (center axis P2 of the second concave portion 122). In this embodiment, the first blade 82 is formed at the boundary between the first inner sloped surface 127 and the outer relay surface 90, and the second blade 84 is formed at the boundary between the second inner sloped surface 128 and the outer relay surface 90.

Figure 18:
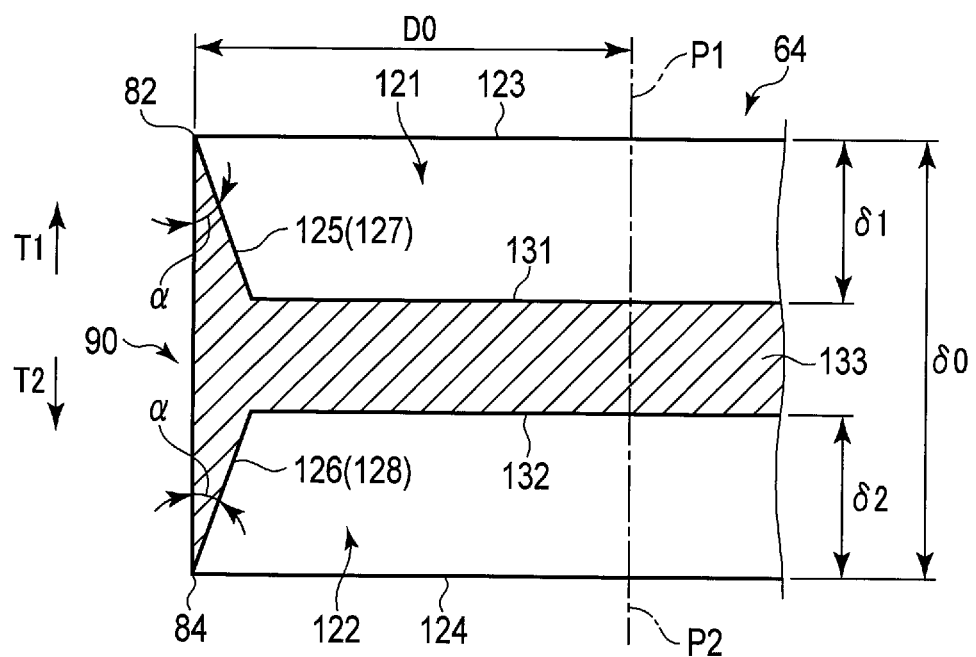
FIG. 18 is a schematic cross-sectional view showing a cross section which passes through an outer relay surface and which is substantially perpendicular to a direction around a center axis of a first concave portion and a second concave portion of the treating portion according to an exemplary embodiment.

FIG. 18 is a view showing a cross section of the treating portion 64 passing through the outer relay surface 90 (blades 82 and 84) and being substantially perpendicular to the direction around the center axis P1 of the first concave portion 121 (center axis P2 of the second concave portion 122). As shown in FIG. 18, in the embodiment, in any cross section which passes through the outer relay surface 90 (blades 82 and 84) and is substantially perpendicular to the axis direction around the center axis P1 of the first concave portion 121, the distance from the center axis P1 of the first concave portion 121 (center axis P2 of the second concave portion 122) to the outer relay surface 90 across the region from the first blade 82 to the second blade 84 is substantially equal to the reference distance (D0) being the distance from the center axis P1 to the first blade 82 (second blade 84). Therefore, in any cross section passing through the outer relay surface 90 and being substantially perpendicular to the direction around the center axis P1 of the first concave portion 121, the distance from the center axis P1 of the first concave portion 121 (center axis P2 of the second concave portion 122) to the outer relay surface 90 across the region from the first blade 82 to the second blade 84 on the second outer surface 74 is kept equal to or less than the reference distance (D0) from the center axis P1 to the first blade 82 (second blade 84). Moreover, in any cross section passing through the outer relay surface 90 and being substantially perpendicular to the direction around the center axis P1 of the first concave portion 121, the distance from the center axis P1 (center axis P2) to the outer relay surface 90 is maximum at each of the first blade 82 and the second blade 84.

Here, the angle formed by each of the first inner sloped surface (first blade-forming surface) 127 and the second inner sloped surface (second blade-forming surface) 128 with respect to the direction along the center axis P1 (center axis P2) is defined as the inner protrusion angle α, and the angle formed by the outer relay surface 90 with respect to the direction along the center axis P1 is defined as the outer protrusion angle β. Each of the inner protrusion angle α and the outer protrusion angle β is a parameter set within a range larger than −90° but smaller than 90°. In the embodiment, since the treating portion 64 is formed as mentioned, the inner protrusion angle α takes a positive value. Further, since the outer relay surface 90 is substantially parallel to the center axis P1 and the center axis P2, the outer protrusion angle β is zero or substantially zero (not shown in FIG. 18). As a result, in this embodiment, as in the aforementioned embodiments, the outer relay surface 90 does not protrude to the side away from the center axis P1 (center axis P2) with respect to the first blade 82 and the second blade 84. Also, the distance δ1 from the first opening 123 to the bottom surface 131 (bottom) of the first concave portion 121 in the direction along the center axis P1 is smaller than the distance δ0 from the first opening 123 of the first outer surface 72 to the second outer surface 74 (second opening 124). Similarly, the distance δ2 from the second opening 124 to the bottom surface 132 (bottom) of the second concave portion 122 in the direction along the center axis P2 is smaller than the distance δ0 from the second opening 124 of the second outer surface 74 to the first outer surface 72 (first opening 123).

As mentioned, in this embodiment, the outer relay surface 90 does not protrude to the side away from the center axis P1 (center axis P2) with respect to the first blade 82 and the second blade 84. Therefore, in this embodiment, as in the aforementioned embodiments, the angle between the bottom surface (116) and the lateral surface (118) in the excised portion (115) of the cartilage (112A) excised by the single abrasion can easily become a substantially right angle, and the lateral surface (118) can easily be formed perpendicular to the bottom surface (116).

In this embodiment, concave portions 121 and 122 are provided instead of the through-hole 76 of the aforementioned embodiment. Thus, the surface in the treating portion 64 perpendicular or substantially perpendicular to the direction along the center axis L of the treating portion 64, that is, the surface perpendicular or substantially perpendicular to the vibrating direction of the treating portion 64 caused by the ultrasonic vibration is more reduced than in the configuration in which the through-hole 76 is provided. By reducing the surface perpendicular or substantially perpendicular to the vibrating direction of the treating portion 64 caused by the ultrasonic vibration, the formation of bubbles caused by the cavitation during the state in which the treating portion 64 inside the liquid is vibrating due to the ultrasonic vibration can be suppressed. Suppressing the formation of bubbles during the treatment caused by the cavitation improves the visibility of the arthroscope 12 and the like.

Figure 14:
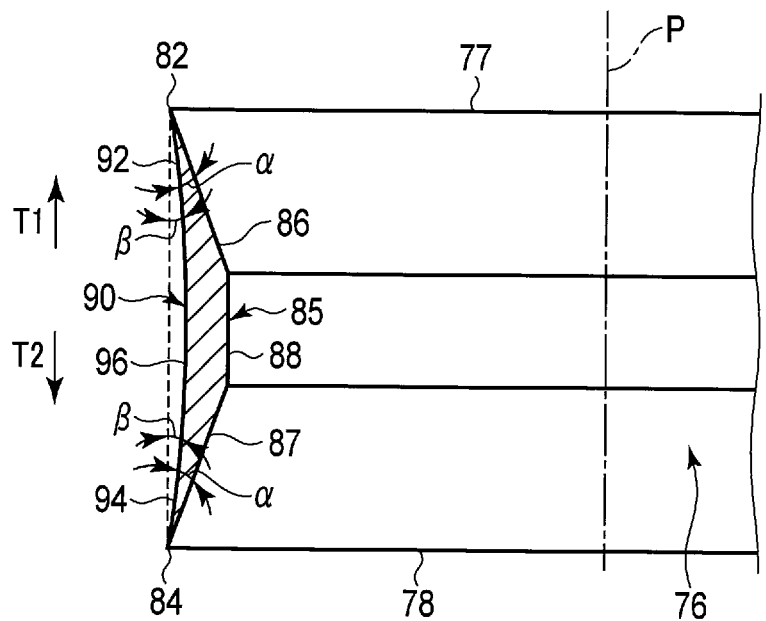
FIG. 14 is a schematic cross-sectional view schematically showing a cross section which passes through an outer relay surface and which is substantially perpendicular to a direction around a center axis of a through-hole of a treating portion according to an exemplary embodiment.

In another exemplary embodiment, as in the embodiment shown in FIG. 14, the outer relay surface 90 is concave to the side approximating the center axis P1 (center axis P2) with respect to the first blade 82 and the second blade 84. In such case as well, in each cross section passing through the outer relay surface 90 and being substantially perpendicular to the direction around the center axis P1 of the first concave portion 121 (center axis P2 of the second concave portion 122), the distance from the center axis P1 (center axis P2) to the outer relay surface 90 across the region from the first blade 82 to the second blade 84 on the second outer surface 74 is kept equal to or less than the reference distance from the center axis P1 to the first blade 82 (second blade 84).

In another exemplary embodiment, the first inner sloped surface 127 does not continue to the bottom surface 131 of the first concave portion 121. In this case, the first inner relay surface 125 includes the inner extending surface (not shown) continuing between the first inner sloped surface 127 and the bottom surface 131, and the first inner relay surface 125 is formed by the first inner sloped surface 127 and the inner extending surface (first inner extending surface). In an embodiment, the inner extending surface between the first inner sloped surface 127 and the bottom surface 131 is substantially parallel to the center axis P1 of the first concave portion 121. Similarly, in another exemplary embodiment, the second inner sloped surface 128 may not continue to the bottom surface 132 of the second concave portion 122. In this case, the second inner relay surface 126 includes the inner extending surface (not shown) continuing between the second inner sloped surface 128 and the bottom surface 132, and the second inner relay surface 126 is formed by the second inner sloped surface 128 and the inner extending surface (second inner extending surface). In an embodiment, the inner extending surface between the second inner sloped surface 128 and the bottom surface 132 is substantially parallel to the center axis P2 of the second concave portion 122.

However, in any of the cases, the distance δ1 from the first opening 123 to the bottom of the first concave portion 121 in the direction along the center axis P1 is smaller than the distance δ0 from the first opening 123 of the first outer surface 72 to the second outer surface 74 (second opening 124). Also, the distance δ2 from the second opening 124 to the bottom of the second concave portion 122 in the direction along the center axis P2 is smaller than the distance δ0 from the second opening 124 of the second outer surface 74 to the first outer surface 72 (first opening 123).

In another exemplary embodiment, only the first blade 82 may be provided and no blade may be formed on the second outer surface 74. In this case, the second concave portion 122 is not provided on the second outer surface 74. However, in such an embodiment as well, the first concave portion 121 concave towards the second outer surface 74 side is formed on the first outer surface 72. Also, the first inner relay surface 125 extends from the first opening 123 to the bottom surface 131, and the outer relay surface 90 extends from the first blade 82 to the second outer surface 74. In this embodiment as well, in each cross section perpendicular to the direction around the center axis P1 of the first concave portion 121 across the region from the first blade 82 to the second outer surface 74, the distance from the center axis P1 to the outer relay surface 90 is kept equal to or less than the reference distance from the center axis P1 to the first blade 82. That is, in any cross section passing through the outer relay surface 90 and being substantially perpendicular to the direction around the center axis P1 of the first concave portion 121, the distance from the center axis P1 to the outer relay surface 90 at the first blade 82 is maximum.

Although in the aforementioned embodiments, examples have been described in which cartilage is excised per the blade (82 and 84) of the treating portion 64 by ultrasonic vibration, the treatment object excised by the treating portion 64 is not limited to cartilage. In other exemplary embodiments, bone such as osteophyte (or bone spur) of the femur 112 as the treatment object is excised using the blade (82 and 84) of the treating portion 64 by causing the treating portion 64 to vibrate as mentioned by using the ultrasonic vibration. The treating portion 64 can also be utilized for treatment of joints other than the knee joint 100, such as ankle joints, shoulder joints and the like.

In the aforementioned embodiments, the ultrasonic probe includes the probe main body (62) to which the ultrasonic vibration generated by the transducer (48) is transmitted, and the treating portion (64) which is provided on the distal side with respect to the probe main body (62) and excises bone or cartilage as the treatment object by the ultrasonic vibration. The treating portion (64) includes the first outer surface (72) facing in the direction intersecting the extending direction of the treating portion (64), and the second outer surface (74) facing a side opposite to a side where the first outer surface (72) faces. The treating portion (64) further has the through-hole (76) penetrating from the first outer surface (72) to the second outer surface (74) or the concave portion (121) concave towards the second outer surface (74) side on the first outer surface (72). The through-hole (76) or the concave portion (121) opens at the opening (77; 123) on the first outer surface (72). The treating portion (64) includes the blade (82) formed along the edge of the opening (77; 123) of the through-hole (76) or the concave portion (121), and the outer relay surface (90) extending from the blade (82) to the second outer surface (74) while facing a side away from the center axis (P; P1) of the through-hole (76) or the concave portion (121). In the cross section perpendicular to the direction around the center axis (P; P1) of the through-hole (76) or the concave portion (121), the distance from the center axis (P; P1) of the through-hole (76) or the concave portion (121) to the outer relay surface (90) across the region from the blade (82) to the second outer surface (74) is kept equal to or less than the reference distance from the center axis (P, P1) to the blade (82).

Additional advantages and modifications will readily occur to those skilled in the art. Therefore, the present disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic probe comprising:
    a probe main body configured to receive ultrasonic vibration generated by a transducer; and
    a treatment portion provided on a distal side with respect to the probe main body, the treatment portion being configured to excise bone or cartilage by the ultrasonic vibration, the treatment portion comprising:
        a first outer surface including a first concave portion,
        a second outer surface facing in a direction opposite to the first outer surface and including a second concave portion, the first concave portion and the second concave portion being coaxially disposed about a center axis that intersects an extending direction of the treatment portion such that the first concave portion and the second concave portion are concave in opposite directions along the center axis,
        a first blade formed along an edge of an opening of the first concave portion,
        a second blade formed along an edge of an opening of the second concave portion, and
        an outer relay surface which extends from the first blade to the second blade and faces away from the center axis, a distance from the center axis of the first and second concave portions to the first blade being greater than or equal to a distance from the center axis to the outer relay surface at a position between the first blade and the second blade,
    wherein:
        the first concave portion includes a first inner relay surface extending from the opening of the first concave portion to a bottom surface of the first concave portion,
        the first inner relay surface includes a first inner sloped surface extending from the opening of the first concave portion toward the bottom surface of the first concave portion, the first inner sloped surface being sloped in a direction from the opening of the first concave portion towards the center axis,
        the second concave portion includes a second inner relay surface extending from the opening of the second concave portion to a bottom surface of the second concave portion, and
        the second inner relay surface includes a second inner sloped surface extending from the opening of the second concave portion towards the bottom surface of the second concave portion, the second inner sloped surface being sloped in a direction from the opening of the second concave portion towards the center axis.

2. The ultrasonic probe according to claim 1, wherein the first blade and the second blade are equal distances from the center axis.

3. The ultrasonic probe according to claim 2, wherein the distance from the center axis to the outer relay surface at a position between the first blade and the second blade is equal to the distance from the center axis to the first blade.

4. The ultrasonic probe according to claim 1, wherein a distance from the opening of the first concave portion to a bottom of the first concave portion is smaller than a distance from the opening of the first concave portion to the second outer surface.

5. The ultrasonic probe according to claim 1, wherein the center axis of the first concave portion and the second concave portion is parallel to a thickness direction of the treatment portion.

6. The ultrasonic probe according to claim 5, wherein the center axis is orthogonal to the extending direction of the treatment portion.

7. The ultrasonic probe according to claim 1, wherein the first blade is formed at a boundary between the first inner sloped surface and the outer relay surface.

8. The ultrasonic probe according to claim 7, wherein the second blade is formed at a boundary between the second inner sloped surface and the outer relay surface.

9. An ultrasonic probe comprising:
    a probe main body configured to receive ultrasonic vibration generated by a transducer; and
    a treatment portion provided on a distal side with respect to the probe main body, the treatment portion being configured to excise bone or cartilage by the ultrasonic vibration, the treatment portion comprising:
        a first outer surface, and
        a second outer surface facing in a direction opposite to the first outer surface,
        a through-hole extending from the first outer surface to the second outer surface along a center axis intersecting an extending direction of the treatment portion, an outer periphery of the through-hole being defined by an inner relay surface extending from a first outer surface opening of the through-hole to a second outer surface opening of the through-hole, the inner relay surface comprising:
- a first inner sloped surface extending from the first outer surface opening of the through-hole towards a second outer surface side, the first inner sloped surface being sloped in a direction from the first outer surface opening of the through-hole towards the center axis, and
- a second inner sloped surface extending from the second outer surface opening of the through-hole towards a first outer surface side, the second inner sloped surface being sloped in a direction from the second outer surface opening of the through-hole towards the center axis,
- a first blade formed along an edge of the first outer surface opening of the through-hole, and
- an outer relay surface which extends from the first blade to the second outer surface and faces away from the center axis, a distance from the center axis of the through-hole to the first blade being greater than or equal to a distance from the center axis to the outer relay surface at a position between the first blade and the second outer surface.

10. The ultrasonic probe according to claim 9, wherein the inner relay surface comprises an inner extending surface extending between the first inner sloped surface and the second inner sloped surface in a direction parallel to the center axis.

11. The ultrasonic probe according to claim 9, wherein:
the treatment portion further comprises a second blade formed along an edge of the second outer surface opening of the through-hole, a distance from the center axis of the through-hole to the second blade being equal to the distance from the center axis of the through-hole to the first blade, and
the outer relay surface extends from the first blade to the second blade.

12. The ultrasonic probe according to claim 11, wherein a distance from the center axis of the through-hole to the outer relay surface at a position between the first blade and the second blade is equal to the distance from the center axis of the through-hole to the first blade.

13. The ultrasonic probe according to claim 11, wherein the second blade is formed at a boundary between the second inner sloped surface and the outer relay surface.

14. The ultrasonic probe according to claim 9, wherein the center axis of the through-hole is orthogonal to the extending direction of the treatment portion.

15. The ultrasonic probe according to claim 9, wherein the first blade is formed at a boundary between the first inner sloped surface and the outer relay surface.

* * * * *